(12) United States Patent
Strommer et al.

(10) Patent No.: US 9,814,889 B2
(45) Date of Patent: Nov. 14, 2017

(54) INJECTABLE SUBCUTANEOUS STRING HEART DEVICE

(71) Applicant: NewPace Ltd., Caesarea (IL)

(72) Inventors: Gera M. Strommer, Haifa (IL); Robert S. Fishel, Delray Beach, FL (US); Avi Broder, Petach Tikva (IL)

(73) Assignee: Newpace Ltd., Caesarea (IL)

( * ) Notice: Subject to any disclaimer, the term of this patent is extended or adjusted under 35 U.S.C. 154(b) by 0 days.

(21) Appl. No.: 14/646,130

(22) PCT Filed: Nov. 21, 2013

(86) PCT No.: PCT/US2013/071338
§ 371 (c)(1),
(2) Date: May 20, 2015

(87) PCT Pub. No.: WO2014/081978
PCT Pub. Date: May 30, 2014

(65) Prior Publication Data
US 2015/0343228 A1 Dec. 3, 2015

Related U.S. Application Data

(60) Provisional application No. 61/844,879, filed on Jul. 11, 2013, provisional application No. 61/765,195, (Continued)

(51) Int. Cl.
*A61N 1/37* (2006.01)
*A61N 1/372* (2006.01)
(Continued)

(52) U.S. Cl.
CPC ......... *A61N 1/37205* (2013.01); *A61M 25/09* (2013.01); *A61N 1/0587* (2013.01);
(Continued)

(58) Field of Classification Search
CPC ...... A61N 1/048; A61N 1/375; A61N 1/3956; A61N 1/0563; A61N 1/3756
See application file for complete search history.

(56) References Cited

U.S. PATENT DOCUMENTS 5,133,353 A 7/1992 Hauser
5,261,400 A 11/1993 Bardy
(Continued)

FOREIGN PATENT DOCUMENTS

CN 101115525 A 1/2008
EP 1631350 A2 3/2006
(Continued)

OTHER PUBLICATIONS

Extended European Search Report dated Jul. 25, 2007 for European Patent Application No. 13857150.0 (9 Pages).
(Continued)

*Primary Examiner* — Michael Carey
*Assistant Examiner* — Natasha Patel
(74) *Attorney, Agent, or Firm* — Brown Rudnick LLP

(57) ABSTRACT

Injectable subcutaneous heart device (ISHD) for regulating arrhythmias in a heart of a patient, including a plurality of linked structures, each one of the linked structures being hollow, an interconnecting bus, a biocompatible coating, at least two electrodes and a plurality of sensors, the interconnecting bus for electrically coupling the linked structures and the biocompatible coating for hermetically sealing and electrically insulating the linked structures, one of the linked structures encapsulating a power source, another one of the linked structures encapsulating at least one capacitor and a third one of the linked structures encapsulating electronics, the electrodes and the sensors being respectively placed on an outer surface of the linked structures located at opposite ends of the ISH D, for detecting arrhythmias and providing (Continued)

electrical shocks to the heart, the electrodes and the sensors being electrically coupled with the interconnecting bus and the ISHD being positioned subcutaneously around the heart.

27 Claims, 14 Drawing Sheets

Related U.S. Application Data filed on Feb. 15, 2013, provisional application No. 61/728,897, filed on Nov. 21, 2012.

(51) Int. Cl.
  *A61N 1/39* (2006.01)
  *A61N 1/05* (2006.01)
  *A61M 25/09* (2006.01)
  *A61N 1/375* (2006.01)

(52) U.S. Cl.
  CPC ......... *A61N 1/3756* (2013.01); *A61N 1/3956* (2013.01); *A61N 1/3987* (2013.01); *A61N 1/0563* (2013.01); *A61N 1/3962* (2013.01)

(56) References Cited

U.S. PATENT DOCUMENTS

| | | | |
|---|---|---|---|
| 5,314,451 A | 5/1994 | Muller | |
| 5,573,551 A | 11/1996 | Lin et al. | |
| 5,645,586 A | 7/1997 | Meltzer | |
| 6,256,541 B1 | 7/2001 | Heil et al. | |
| 6,647,292 B1 | 11/2003 | Bardy et al. | |
| 6,721,597 B1 | 4/2004 | Bardy et al. | |
| 7,069,075 B2 | 6/2006 | Olson | |
| 7,363,083 B2 | 4/2008 | Bardy et al. | |
| 7,617,007 B2 | 11/2009 | Williams et al. | |
| 7,684,864 B2 | 3/2010 | Olson et al. | |
| 7,835,790 B2 | 11/2010 | Ostroff et al. | |
| 7,894,894 B2 | 2/2011 | Stadler et al. | |
| 7,894,915 B1 | 2/2011 | Chitre et al. | |
| 7,899,554 B2 | 3/2011 | Williams et al. | |
| 7,937,148 B2 | 5/2011 | Jacobson | |
| 8,135,459 B2 | 3/2012 | Bardy et al. | |
| 8,147,486 B2 | 4/2012 | Honour et al. | |
| 8,260,415 B2 | 9/2012 | Donofrio | |
| 8,311,633 B2 | 11/2012 | Ransbury et al. | |
| 8,359,094 B2 | 1/2013 | Bonner et al. | |
| 8,483,841 B2 | 7/2013 | Sanghera et al. | |
| 8,512,254 B2 | 8/2013 | Donofrio | |
| 8,644,926 B2 | 2/2014 | Ostroff et al. | |
| 8,718,760 B2 | 5/2014 | Bardy et al. | |
| 8,768,458 B2 | 7/2014 | Bardy et al. | |
| 2003/0045892 A1 | 3/2003 | Kaladelfos | |
| 2004/0176818 A1 | 9/2004 | Wahlstrand et al. | |
| 2004/0210292 A1 | 10/2004 | Bardy et al. | |
| 2005/0043765 A1 | 2/2005 | Williams et al. | |
| 2006/0247688 A1* | 11/2006 | Olson | A61N 1/3968 607/5 |
| 2008/0167702 A1 | 7/2008 | Ransbury et al. | |
| 2008/0183230 A1 | 7/2008 | Kemmetmueller et al. | |
| 2008/0294210 A1* | 11/2008 | Rosero | A61N 1/05 607/5 |
| 2009/0076401 A1 | 3/2009 | Mazar et al. | |
| 2009/0149902 A1* | 6/2009 | Kumar | A61N 1/0587 607/4 |

FOREIGN PATENT DOCUMENTS

| | | |
|---|---|---|
| EP | 2510973 A2 | 10/2012 |
| WO | 2003/002198 A2 | 1/2003 |
| WO | 2004/028628 A1 | 4/2004 |
| WO | 2004/108212 A2 | 12/2004 |
| WO | 2007103262 A2 | 9/2007 |
| WO | 2012/013360 A1 | 2/2012 |
| WO | 2014/081978 A1 | 5/2014 |

OTHER PUBLICATIONS

First Office Action of State Intellectual Property Office dated Feb. 25, 2016, for Chinese Patent Application No. 2013800690053 (19 Pages) which claims priority to PCT/US2013/071338.

International Search Report and Written Opinion of the International Searching Authority dated Jan. 7, 2016 for International Application No. PCT/IL2015/050895 (11 Pages).

International Search Report and Written Opinion for International application No. PCT/US2013/071338 filed Nov. 21, 2013 and dated Feb. 4, 2104, (11 pages).

* cited by examiner

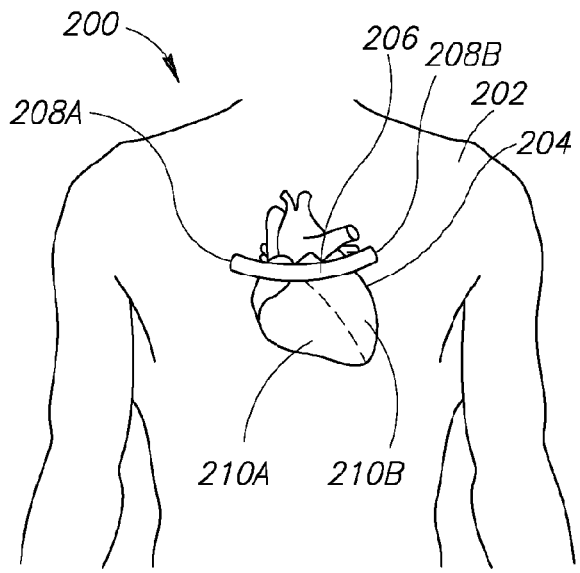
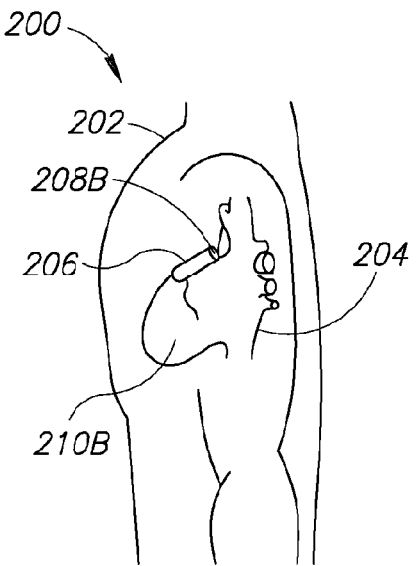
FIG.4A  FIG.4B
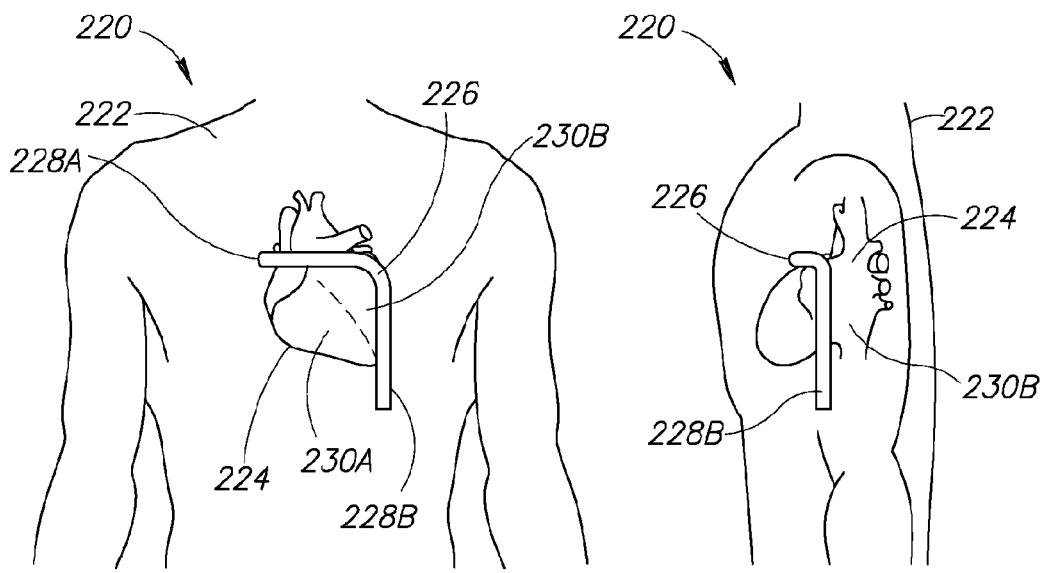
FIG.4C  FIG.4D

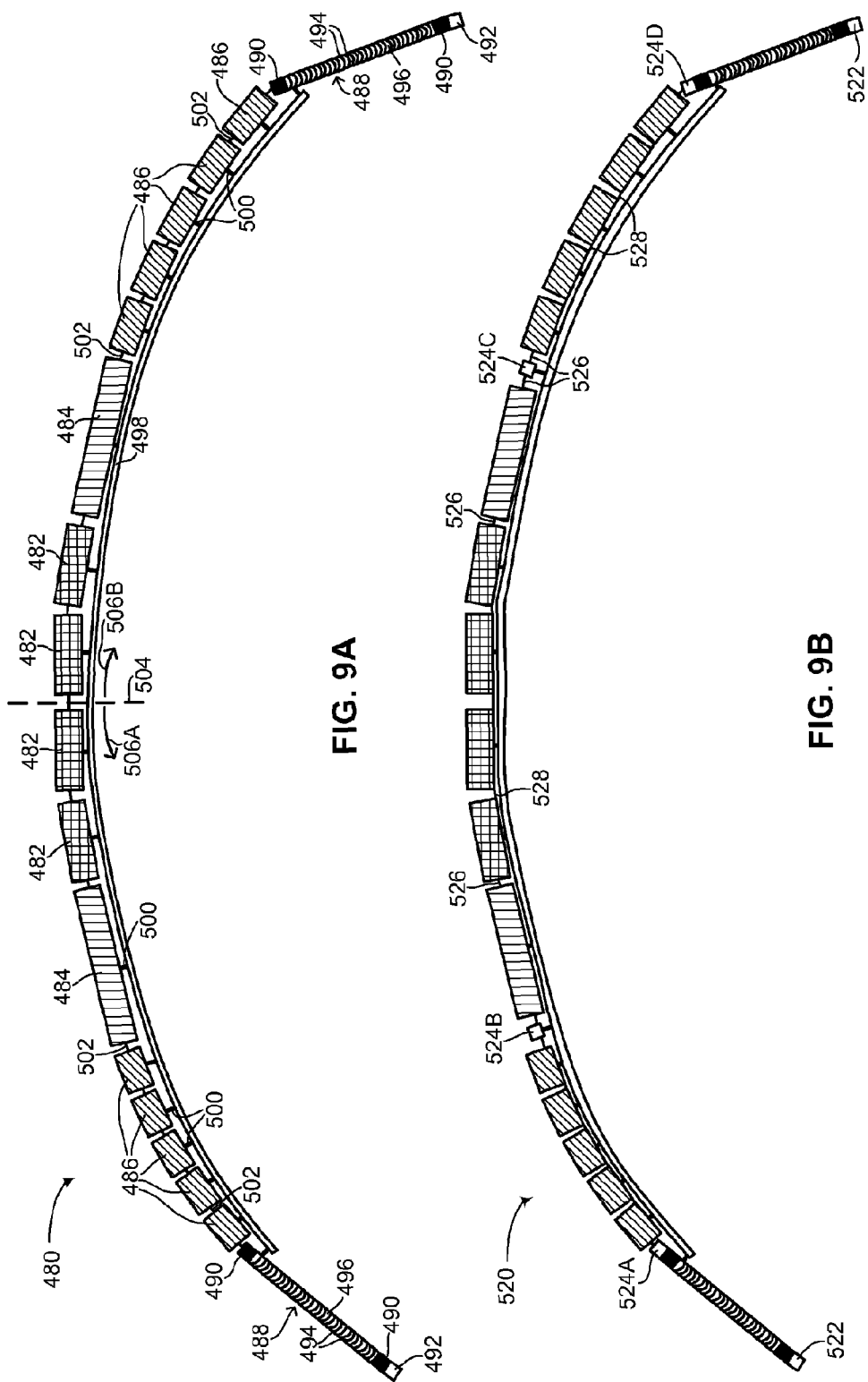

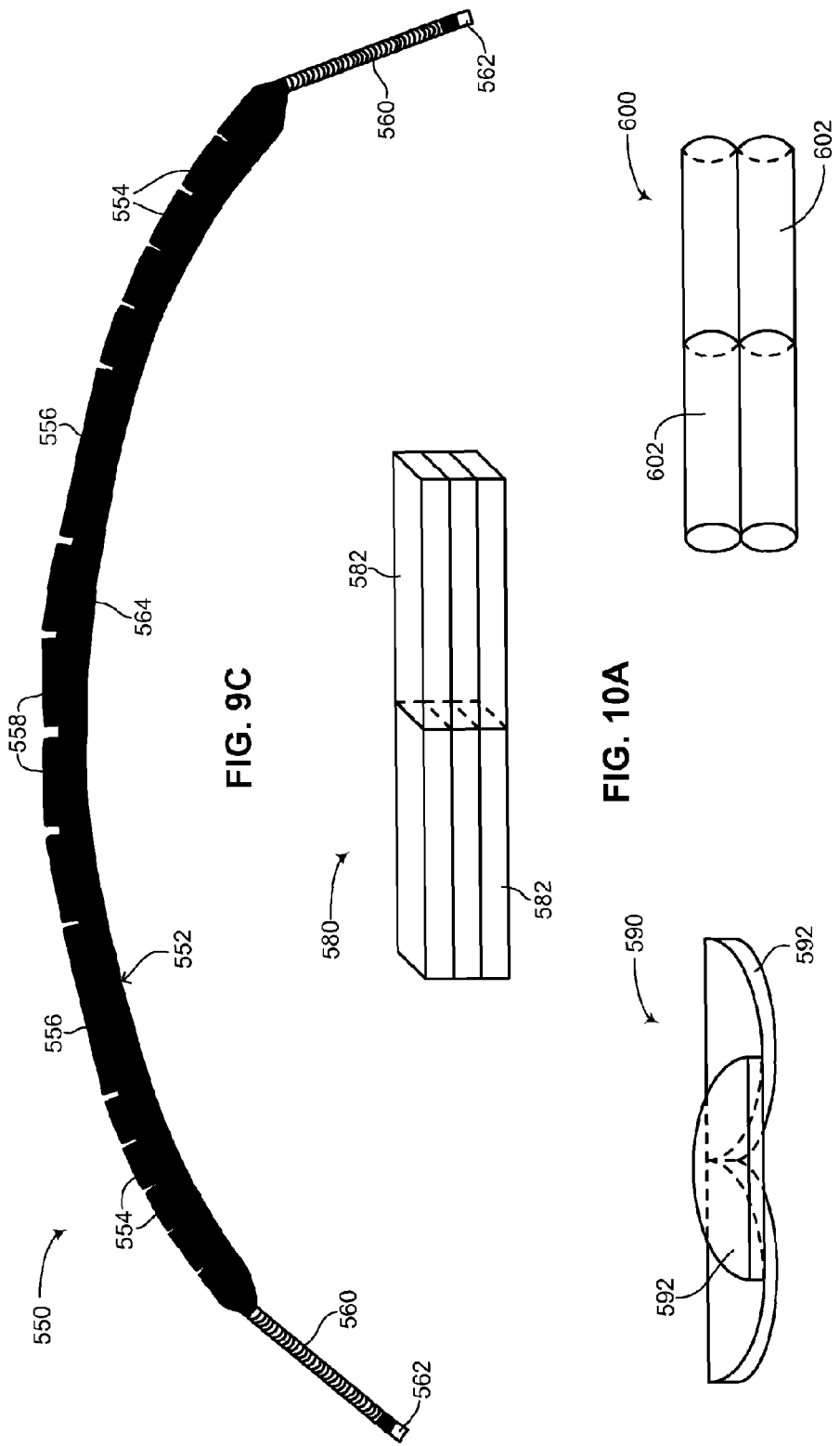

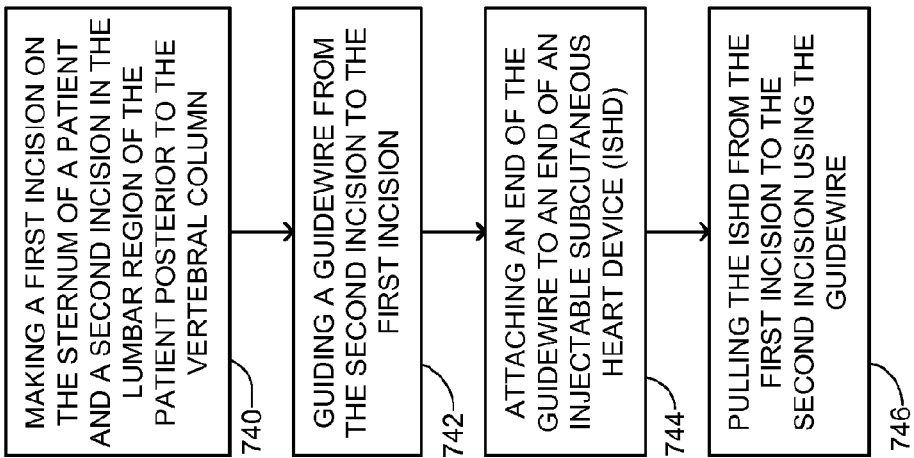
FIG. 13C
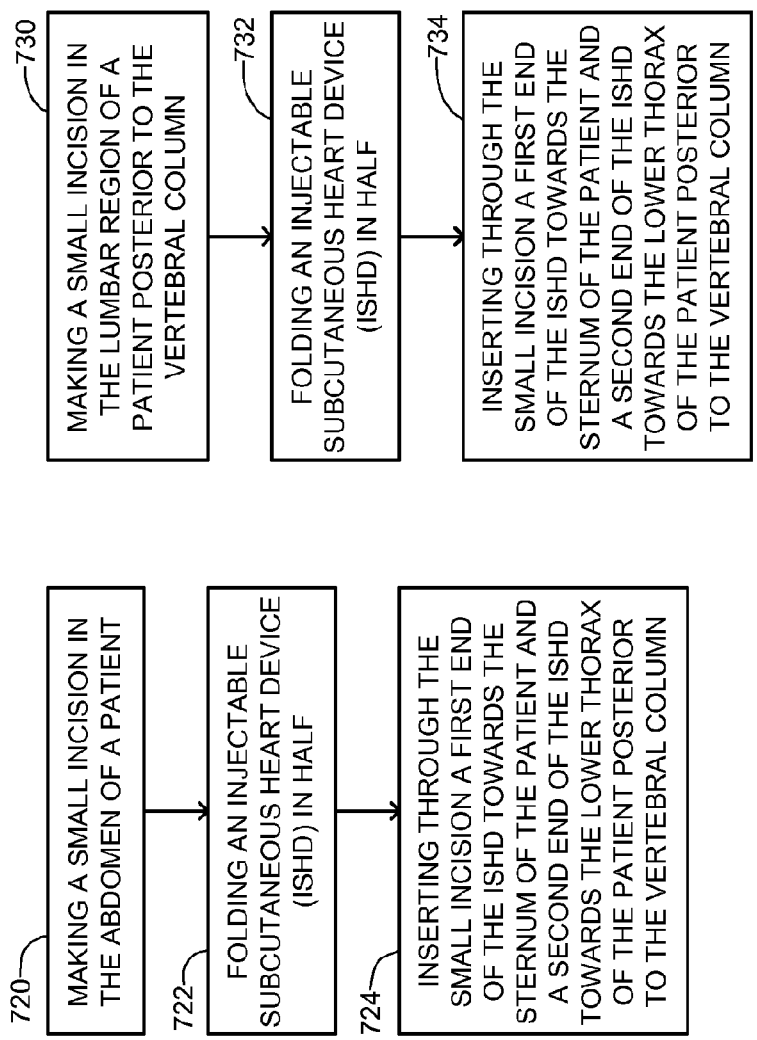
FIG. 13B
FIG. 13A

INJECTABLE SUBCUTANEOUS STRING HEART DEVICE

CROSS REFERENCE

This application claims priority from the following U.S. provisional patent applications: U.S. 61/728,897, filed on Nov. 21, 2012, U.S. 61/765,195, filed on Feb. 15, 2013 and U.S. 61/844,879, filed Jul. 11, 2013. Each of these three applications is incorporated herein by reference.

FIELD OF THE DISCLOSED TECHNIQUE

The disclosed technique relates to heart devices, in general, and pacemakers and implantable cardioverter defibrillators and their methods of use, in particular.

BACKGROUND OF THE DISCLOSED TECHNIQUE

An arrhythmia is a medical condition in which there exists a problem with the rate or rhythm of the heartbeat usually due to abnormal electrical activity in the heart. More specific types of arrhythmia include when the heart beats too fast (known as tachycardia), too slow (known as bradycardia) or with an irregular rhythm (known as cardiac fibrillation). Two general devices are known in the art for helping people who experience arrhythmias. One is known as a pacemaker, the other is known as an implantable cardioverter defibrillator (herein abbreviated ICD). Pacemakers are implantable devices which continuously measure the heartbeat and electrical activity in the heart. Pacemakers can detect irregularities in the heartbeat, i.e. arrhythmias, and are programmed to provide electrical signals to the heart to restore its normal beating rhythm.

Reference is now made to FIG. 1, which is a schematic illustration of a pacemaker implanted in a patient, generally referenced 10, as is known in the art. As shown in FIG. 1, a pacemaker 12 is implanted in a patient 14, having a heart 16 and a ribcage 18. Pacemaker includes two main components, a can 20 and electrical leads 22. Can 20 includes a power source (not shown), such as a battery, as well as an electronic device (not shown) for monitoring the electrical activity in the heart and for providing electrical signals to the heart when aberrant rhythms of the heart are detected. Can 20 is usually implanted in patient 14 via a surgical procedure on his left side adjacent to and below the clavicle bone (also known as the collarbone), as shown by an arrow 24 in FIG. 1. Electrical leads 22 are coupled with the electronic device in can 20 at one end and are coupled with heart 16 at the other end, the electrical leads being inserted through the subclavian vein (not shown) and the vena cava (not shown). Electrical leads 22 are typically implanted in patient 14 by inserting them percutaneously through his vena cava (not shown). Once attached to heart 16, they are coupled with can 20. Electrical leads 22 are usually flexible and provide electrical signals of heart 16 to the electronic device in can 20 as well as providing electrical signals from the electronic device to heart 16. Typically, electrical leads 22 are implanted in right ventricle 26 and right atrium 28 of heart 16.

ICDs are similar to pacemakers and include similar components, such as a can and electrical leads; thus pacemaker 12 in FIG. 1 could also be an ICD. An ICD differs slightly from a pacemaker in that its can includes a power source, electronics, electrical leads as well as at least one capacitor. The difference between an ICD and a pacemaker is that an ICD can deliver a high voltage electric shock to the heart to terminate an otherwise potentially fatal cardiac tachyarrhythmia. A pacemaker is generally limited to treating bradyarrhythmias which can be treated with a significantly lower voltage electric impulse. The presence of at least one capacitor in an ICD accounts for its difference in function from a pacemaker as the at least one capacitor enables a significantly higher electrical shock to be built up and delivered to the heart. An additional function of an ICD is to send the heart an electrical shock in case of ventricular fibrillation (herein abbreviated VF) and in order to prevent cardiac arrest, i.e., aborted sudden death. The electrical energy required for the electrical shock is built up and stored in the at least one capacitor. ICDs exist as standalone devices yet are also manufactured having the functionality of a pacemaker. In addition, cardiac resynchronization therapy defibrillators (herein abbreviated as CRT-D) include a third electrode allowing for simultaneous pacing of both the right and left ventricles of the heart.

As mentioned above, ICDs, similar to pacemakers, constantly monitor the rate and rhythm of the heart and deliver therapies to the heart by way of an electrical shock. In the case of an ICD, electrical shocks are provided to the heart when the measured electrical activity of the heart exceeds a preset number. State of the art ICDs can distinguish different types of aberrant electrical activity in the heart, such as VF, when the heart contracts irregularly, versus ventricular tachycardia (herein abbreviated VT), when the heart beats regularly but significantly faster than normal. In the case of VT, such ICDs may send electrical signals to the heart to try and pace the heart faster than its intrinsic heart rate in an attempt to stop the tachycardia before it progresses to VF. This technique is known in the art as fast-pacing, overdrive pacing or anti-tachycardia pacing (herein abbreviated ATP). As is known to workers skilled in the art, ATP is only effective if the underlying rhythm of the heart is ventricular tachycardia. ATP is never effective if the heart is already experiencing ventricular fibrillation and thus lacks a consistent heart rate. State of the art ICDs use a combination of various methods to determine if received electrical signals from the electrical leads represent a normal rhythm of the heart, ventricular tachycardia or ventricular fibrillation. It is noted that the placement of an ICD in the body of a patient is similar to that of a pacemaker, however in the case of a CRT-D device, the electrical leads can also be implanted in the left side of the heart via the coronary sinus (not shown) of the heart. This is shown in FIG. 1 as an electrical lead 30, denoted by a dashed line. In addition, is it noted that state of the art ICDs exist in which the electrical leads of an ICD are not inserted into the heart but are positioned subcutaneously above the heart. Such ICDs provide improved safety to a patient since the insertion of the electrical leads of the ICD does not involve any intervention with the heart.

ICDs and pacemakers are known in the art. Major manufacturers of these devices include Medtronic, Boston Scientific, St. Jude Medical, Cameron Health (recently acquired by Boston Scientific), Biotronic and Sorin Group. For example, U.S. Pat. No. 7,363,083 to Bardy et al., assigned to Cameron Health, entitled "Flexible subcutaneous implantable cardioverter-defibrillator" is directed to an implantable cardioverter-defibrillator for subcutaneous positioning over a patient's ribcage. The implantable cardioverter-defibrillator includes a housing which conforms to the patient's ribcage when subcutaneously positioned, an electrode disposed upon a portion of the housing and an electrical circuit located within the housing. The electrical circuit is electrically coupled to the electrode. The implantable cardioverter-defibrillator also includes a battery and a capacitor. The electrical circuitry is configured to detect an abnormal heart rhythm, to charge the capacitor, and to discharge the capacitor to provide a cardioversion/defibrillation shock to the heart. According to another embodiment, the cardioverter-defibrillator also includes a first structural portion for supporting a first cardioversion/defibrillation electrode, which is adapted to be implanted at a first subcutaneous implantation site about the patient's thorax and is also adapted to direct the first cardioversion/defibrillation electrode towards the patient's heart. The cardioverter-defibrillator also includes a second cardioversion/defibrillation electrode, which is adapted to be implanted at a second subcutaneous implantation site about the patient's thorax and is adapted to direct the second cardioversion/defibrillation electrode towards the patient's heart. A connecting structure includes one or more conductors for connecting the first and second structural portions together. The components of the implantable cardioverter/defibrillator are distributed between the first and second structural portions. The components may also be distributed between the one or more conductors of the connecting structure. The plurality of components is interconnected to enable the generation and delivery of cardioversion/defibrillation shocks between the first and second cardioversion/defibrillation electrodes. It is noted that in this patent, the electrodes are implanted subcutaneously however a can is still used to hold the battery, capacitor and electrical circuitry. The can is also used as a contact point for the cardioverter-defibrillator.

U.S. Pat. No. 7,684,864 to Olson et al., assigned to Medtronic, entitled "Subcutaneous cardioverter-defibrillator" is directed to a subcutaneous implantable cardioverter-defibrillator (ICD) which is entirely implantable subcutaneously with minimal surgical intrusion into the body of a patient. The ICD provides distributed cardioversion-defibrillation sense and stimulation electrodes for delivery of cardioversion-defibrillation shock and pacing therapies across the heart when necessary. In one configuration, a hermetically sealed housing is included with one or optionally two subcutaneous sensing and cardioversion-defibrillation therapy delivery leads. In another configuration, two hermetically sealed housings interconnected by a power/signal cable are provided. The housings are generally dynamically configurable to adjust to varying rib structure and associated articulation of the thoracic cavity and muscles. The housings may optionally be flexibly adjusted for ease of implant and patient comfort. In one embodiment, the ICD is electrically coupled to one or more elongated, coil-type high voltage electrodes with the electrodes disposed in a location providing defibrillation vectors covering adequate mass of myocardial tissue to achieve defibrillation and deliver pacing therapy. In another embodiment, more than one high voltage electrode is implemented with the ICD and is connected to all the electrodes. The one or more high voltage electrodes may include a set of coil electrodes disposed in an orientation relative to a patient's heart that provides several different therapy delivery vectors there between. Other state of the art ICDs are described in the following patents: U.S. Pat. Nos. 6,647,292, 7,069,075, 7,835,790 and 8,135,459, all assigned to Cameron Health, U.S. Pat. No. 5,573,551, assigned to Intermedics, U.S. Pat. No. 8,147,486, assigned to St. Jude Medical, U.S. Pat. No. 5,314,451, assigned to Medtronic, and U.S. Pat. No. 7,937,148, assigned to Nanostim.

SUMMARY OF THE DISCLOSED TECHNIQUE

The disclosed technique provides for a novel injectable subcutaneous spine-shaped heart device, a novel introducer for aiding in implanting the injectable subcutaneous spine-shaped heart device into a patient and a novel method for implanting the injectable subcutaneous spine-shaped heart device in a patient, which overcome the disadvantages of the prior art. According to one embodiment of the disclosed technique there is thus provided an injectable subcutaneous heart device (ISHD) for regulating arrhythmias in a heart of a patient, including a plurality of linked structures, an interconnecting bus, a biocompatible coating, at least two electrodes and a plurality of sensors. Each one of the linked structures is hollow, with the interconnecting bus for electrically coupling the plurality of linked structures and the biocompatible coating for hermetically sealing and electrically insulating the plurality of linked structures. A first one of the plurality of linked structures encapsulates a power source, a second one of the plurality of linked structures encapsulates at least one capacitor and a third one of the plurality of linked structures encapsulates electronics. The two electrodes are respectively placed on an outer surface of at least two different ones of the plurality of linked structures located at opposite ends of the ISHD, for providing electrical shocks to the heart for regulating the arrhythmias. At least two of the sensors are located on an outer surface at opposite ends of the ISHD, for detecting the arrhythmias in the heart. The two electrodes and the plurality of sensors are electrically coupled with the interconnecting bus. The power source provides power to the electronics and provides electrical energy to the capacitor which stores electrical energy and discharges the electrical energy to the two electrodes when an arrhythmia is detected in the heart. The heart device is positioned subcutaneously around the heart.

According to another embodiment of the disclosed technique there is thus provided an injectable subcutaneous heart device (ISHD) for regulating arrhythmias in a heart of a patient, including a plurality of vertebrae-like structures, an interconnecting bus, a biocompatible coating, at least two electrodes and a plurality of sensors. Each one of the vertebrae-like structures is hollow. The interconnecting bus is for electrically coupling the plurality of vertebrae-like structures. The biocompatible coating is for hermetically sealing and electrically insulating the plurality of vertebrae-like structures. A first one of the plurality of vertebrae-like structures encapsulates a power source, a second one of the plurality of vertebrae-like structures encapsulates at least one capacitor and a third one of the plurality of vertebrae-like structures encapsulates electronics. The two electrodes are respectively placed on an outer surface of at least two different ones of the plurality of vertebrae-like structures located at opposite ends of the ISHD, for providing electrical shocks to the heart for regulating the arrhythmias. At least two of the sensors are located on an outer surface at opposite ends of the ISHD, for detecting the arrhythmias in the heart. The two electrodes and the plurality of sensors are electrically coupled with the interconnecting bus. The power source provides power to the electronics and provides electrical energy to the capacitor which stores electrical energy and discharges the electrical energy to the two electrodes when an arrhythmia is detected in the heart. The heart device is positioned subcutaneously around the heart.

According to a further embodiment of the disclosed technique there is thus provided an injection device for subcutaneously inserting a heart device including an elongated cylindrical shape, including a proximal end and a distal end. The distal end includes a sharp tip, for inserting the injection device subcutaneously. The injection device is hollow and has a diameter substantially equal to a diameter of the heart device.

According to another embodiment of the disclosed technique there is thus provided a method for subcutaneously injecting a heart device in a patient, the heart device including a plurality of linked structures having a spine-like shape, using an injection device including a hollow elongated cylindrical shape, the injection device having a diameter smaller than a diameter of the heart device, the injection device further including a gap, running along a length of the elongated cylindrical shape. The method includes the procedures of making a first incision in the vicinity of the sternum of the patient and making a second incision in the lumbar region of the patient posterior to the vertebral column of the patient. The injection device is then inserted through the first incision to the second incision. A guidewire is then guided through the injection device via the second incision to the first incision. The heart device is then coupled with an end of the guidewire. The guidewire is pulled through the injection device, thereby pulling the heart device through the injection device from the first incision to the second incision and positioning the heart device in the patient. The guidewire is the detached from the heart device and the injection device is removed from the second incision. Finally the first incision and the second incision are sutured up.

BRIEF DESCRIPTION OF THE DRAWINGS

The disclosed technique will be understood and appreciated more fully from the following detailed description taken in conjunction with the drawings in which:

FIGS. 4A and 4B are schematic illustrations of a first implanting configuration of the injectable subcutaneous string heart device of FIG. 2A, constructed and operative in accordance with a further embodiment of the disclosed technique;

FIGS. 4C and 4D are schematic illustrations of a second implanting configuration of the injectable subcutaneous string heart device of FIG. 2A, constructed and operative in accordance with another embodiment of the disclosed technique;

FIGS. 9A and 9B are schematic illustrations of another injectable subcutaneous heart device, constructed and operative in accordance with another embodiment of the disclosed technique;

FIG. 9C is a schematic illustration of the injectable subcutaneous heart device of FIG. 9A with a coating, constructed and operative in accordance with a further embodiment of the disclosed technique;

FIGS. 10A, 10B and 10C are schematic illustrations of different capacitor designs for use in the injectable subcutaneous heart device of FIG. 9A, constructed and operative in accordance with another embodiment of the disclosed technique;

FIGS. 13A-13D are schematic illustrations of various methods for implanting an injectable subcutaneous heart device, operative in accordance with a further embodiment of the disclosed technique.

DETAILED DESCRIPTION OF THE EMBODIMENTS

Figure 1:
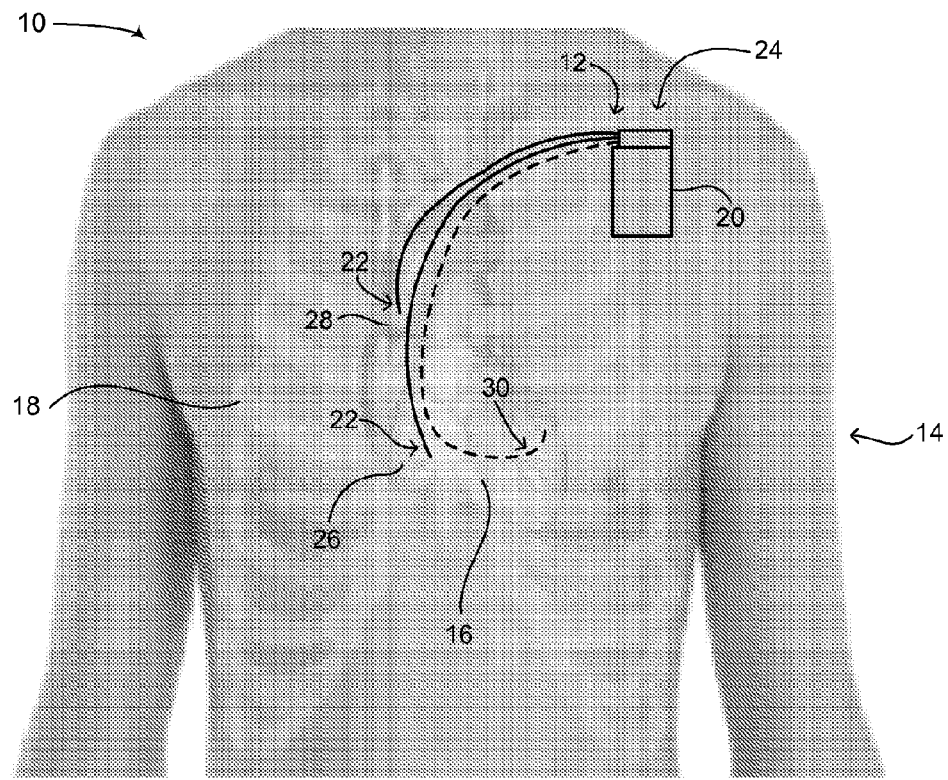
FIG. 1 is a schematic illustration of a pacemaker implanted in a patient, as is known in the art.

The disclosed technique overcomes the disadvantages of the prior art by providing a novel injectable subcutaneous string heart device (herein referred to simply as an ISSHD) and a novel injectable subcutaneous heart device (herein referred to simply as an ISHD) both of which can function as a defibrillator, emergency pacemaker or both. The disclosed technique integrates the can and its internal contents, such as a power source, electronics and at least one capacitor, and the electrical leads of prior art ICDs into a single device having a string shape. Due to the shape of the ISSHD of the disclosed technique, the ISSHD can be injected and positioned subcutaneously around the heart of a patient in a minimally invasive manner. The ISSHD of the disclosed technique thus does not require electrical leads to be coupled with the heart, does not require a separate can to hold the device electronics and a power source, and does not leave a disfiguring bump on the chest of a patient, as is typical in prior art ICDs which include both a can and electrical leads. The ISSHD of the disclosed technique is thus also easily implanted and easily removed from the patient and is cost effective to manufacture. The cost effectiveness of the disclosed technique is due to a number of factors. First, the ISSHD of the disclosed technique is relatively simple in functionality, thus making the ISSHD cost effective. Second, since the ISSHD integrates all its elements into a single component, various packaging and manufacturing costs can be reduced as compared to a system which includes multiple components that need to be manufactured and packaged separately. Third, as explained in greater detail below, since the ISSHD of the disclosed technique is injected subcutaneously, the implantation procedure can be performed using only local anesthetics and in a clinic by a single physician. Such an implantation procedure is very cost effective as compared to prior art ICD implantation procedures which require general anesthetics in an operating room in a hospital, usually staffed by multiple personnel. The disclosed technique thus also saves on the costs of staying in a hospital as well as the cost of care in a hospital. Fourth, since the ISSHD of the disclosed technique is a single device injected subcutaneously, its removal, its replacement, or both, are relatively simple to execute, as explained below, and is thus more cost effective than the removal and/or replacement of an implantable ICD. The removal and/or replacement of an implantable ICD also carries with it higher chances of associated complications since intra cardiac leads need to be removed. The chances of such complications are significantly reduced according to the disclosed technique due to the ISSHD being positioned subcutaneously around the heart of a patient. The ISSHD of the disclosed technique can be easily checked by the patient or by a medical practitioner, thus making it easy to maintain. In addition, the ISSHD of the disclosed technique includes a power source which is rechargeable using energy transfer methods, thus enabling the ISSHD of the disclosed technique to exhibit a substantially long lifetime of usage. For example, state of the art ICDs may require a battery replacement every 5-7 years. In such ICDs, the can needs to be replaced under a full surgical procedure. According to the disclosed technique, the power source can be recharged a plurality of times, enabling the ISSHD of the disclosed technique to operate continuously for years. In some embodiments of the disclosed technique, the power source of the disclosed technique can be recharged remotely such that the ISSHD does not need to be removed from the patient in order to recharge the power source. In other embodiments of the disclosed technique, even in the event that the power source in the ISSHD of the disclosed technique needs to be replaced, since the ISSHD is injected subcutaneously, it can be easily removed and reinserted (for example, with a new battery) without requiring a full surgical procedure.

In general, the terms "string shape," "flexible string shape" and "string-like shape" as used herein with reference to the ISSHD of the disclosed technique refers to any type of injectable medical device having the following characteristics:
- can provide any known stimulation type therapy to the heart, wherein the heart, or a part thereof, is stimulated via electrical impulses;
- is embodied as a single unit, including a power source, electrodes and any other electronics (such as a CPU, at least one capacitor and the like) required to provide the electrical impulses as stimulation (thus not having a separate can and leads configuration as described in the prior art);
- can be positioned inside a patient subcutaneously or percutaneously;
- has a generally tubular or cylindrical shape with a cross-sectional shape having any known curvature. For example, the cross-sectional shape may be a circle, an ellipse or a closed curve. The cross-sectional shape may also be any conic section having an eccentricity ranging from 0 to 1. In addition, the cross-sectional shape may vary or change over length, being different at a distal end as compared to a proximal end of the ISSHD.

Figure 2A:
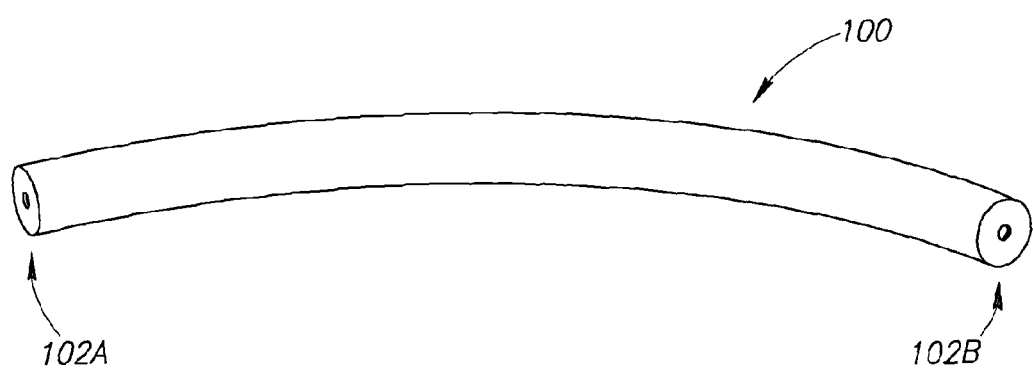
FIG. 2A is a schematic perspective illustration of an injectable subcutaneous string heart device, constructed and operative in accordance with an embodiment of the disclosed technique.
Figure 2B:
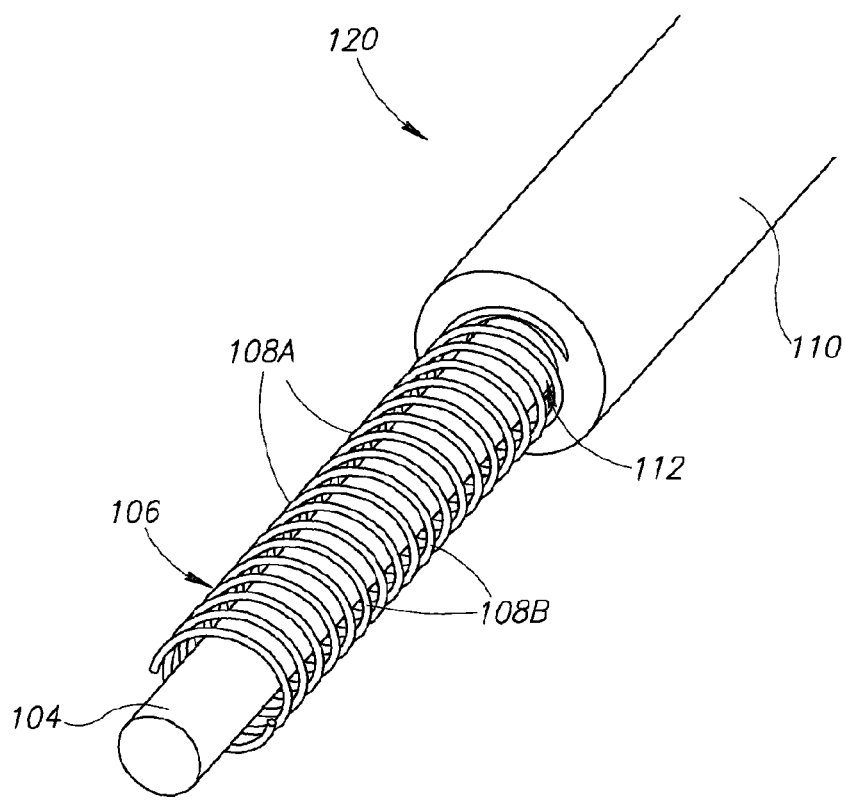
FIG. 2B is a schematic perspective cutaway illustration of the injectable subcutaneous string heart device of FIG. 2A, constructed and operative in accordance with another embodiment of the disclosed technique.

Reference is now made to FIG. 2A, which is a schematic perspective illustration of an injectable subcutaneous string heart device, generally referenced 100, constructed and operative in accordance with an embodiment of the disclosed technique. As shown, ISSHD 100 has an elongated cylindrical shape and includes two ends 102A and 102B. Ends 102A and 102B are explained in greater detail below in FIG. 2B. ISSHD 100 is made from a strong flexible material, such as woven carbon fiber, plastic, silicon and the like. As such, ISSHD 100 can be maneuvered subcutaneously within a patient (not shown). ISSHD 100 has a hollow shape and includes an inner cylinder (shown in FIG. 2B) and an outer cylinder (also shown in FIG. 2B). The space (not shown) between the inner cylinder and the outer cylinder is hollow. Within that space, elements similar to the elements of a prior art ICD are positioned, such as a power source (not shown), at least one capacitor (not shown) or a plurality of capacitors (not shown), electronics (not shown) and electrical leads (not shown). The outer cylinder is substantially a sheath which covers the inner cylinder. All this is shown in greater detail below in FIG. 2B. It is also noted that in one embodiment, as shown in FIG. 2B, the electrical leads may form part of the outer cylinder and are not placed within the aforementioned space.

Each one of ends 102A and 102B of ISSHD 100 includes a circular shaped electrical lead (not shown in FIG. 2A) which is positioned between the inner cylinder and the outer cylinder. The electrical leads are used for monitoring the electrical activity of the heart (not shown) of the patient as well as the heartbeat. The electrical leads provide the monitored electrical activity of the heart and the heartbeat to the electronics, which may include integrated circuits (not shown), logic and analog components (not shown), a separate integrated CPU (not shown), an integrated CPU within an application specific integration circuit (herein abbreviated ASIC) (not shown) and the like, for assessing the condition of the heart and for deciding if electric shocks should be provided to the heart or not. The electronics are powered by a power source which is also used to build up charge on the at least one capacitor. If electric shocks need to be provided to the heart, the electronics provide the electrical energy stored in the at least one capacitor to the electrical leads which provide the electric shocks to the heart. According to the disclosed technique, ISSHD 100 can provide monophasic (or uniphasic) and biphasic electrical shocks to the heart. In an embodiment, the waveform (biphasic or monophasic) provided by ISSHD 100 may be programmable or non-programmable (i.e., hardwired). For example, ISSHD 100 may only provide biphasic electric shocks which in general are more effective in most circumstances of arrhythmias and also require less power than a monophasic electric shock. The detection rate of ISSHD 100, which is the rate at which ISSHD 100 detects the heart rate of the heart may be programmable by a medical profession or may be hardwired. For example, the detection rate may be set at 200 beats per minute (herein abbreviated BPM). If the detection rate is slower than 200 BPM, then non-fatal arrhythmias may be detected by ISSHD 100 and inappropriate therapies (i.e., electric shocks) may be applied by ISSHD 100 to the heart of the patient. In addition, if the heart of the patient is beating faster than 200 BPM for any reason, even if it is not immediately fatal such as atrial fibrillation, then an electric shock from ISSHD 100 may likely benefit the patient. In addition, ISSHD 100 can provide defibrillating shocks as well as pacing shocks to the heart, depending on the monitored electrical activity of the heart and the heartbeat.

In general, the electronics used for monitoring the activity of the heart, including the heartbeat and the electrical activity of the heart, as well as activating and controlling the electric shocks provided to the heart are miniaturized. This enables the electronics to be positioned in the space between the inner cylinder and the outer cylinder. In addition, substantially small batteries are used as a power source, along with at least one substantially small capacitor for storing built up electrical charge. The size of the power source and the at least one capacitor enables the required volume and configuration to encapsulate these elements to be significantly reduced as compared to the prior art and allows for these elements to be spread along the elongated cylindrical shape of ISSHD 100. For example, ISSHD 100 may be between 30-40 centimeters in length, with the outer cylinder having a diameter of 5-6 millimeters or less and the inner cylinder having a diameter of 1-2 millimeters or less, thereby leaving a cylindrical space having a thickness of 4-5 millimeters and a length of approximately 35 centimeters for encapsulating the elements of ISSHD 100. Most of this cylindrical space can be used to position circular leaf-shaped thin film batteries or other thin shape batteries attached to one another, each having a hollow center with a diameter of approximately 1 millimeter or less. The hollow center essentially leaves space for the inner cylinder or forms the space of the inner cylinder, which can be used in conjunction with a medical stylet or stiletto, for inserting ISSHD 100 inside a patient during its implantation procedure. This is described in greater detail below in FIG. 6A. It is noted that other battery shapes are possible, for example coin-shaped batteries. The power source of the disclosed technique may provide an electric shock of anywhere between 800 volts and up to approximately 3000 volts. The voltage which the power source provides is dependent on how much energy should be provided to the heart, which itself is dependent on the electrical impedance of the patient. In general, however, for defibrillation, the higher the voltage, the more efficient the defibrillation is. For example, if 100 joules of energy is to be provided to the heart then a capacitor having a capacitance of 132 microfarads can be used which can store up to approximately 1231 volts. These numbers are based on the formula $$E = \frac{1}{2} * C * V^2 \tag{1}$$

where E is the energy stored in a capacitor in joules, C is the capacitance of the capacitor in farads and V is the voltage stored in capacitor in volts.

Other combinations of specific capacitance and energy provided to the heart are possible and are a matter of design choice. In addition, the electronics of the disclosed technique may include a circuit for increasing the voltage provided by the power source and for converting stored energy from AC to DC and DC to AC. Due to the significantly small size of the power source used, ISSHD 100 may only be able to provide a limited number of electrical shocks, such as fifty shocks, to the heart. According to one embodiment of the disclosed technique, the power source of ISSHD 100 is rechargeable. As such, ISSHD 100 may be able to provide an almost limitless number of electrical shocks to the heart, provided ISSHD 100 is periodically recharged. The power source may be a power source which can be recharged wirelessly using known energy transfer methods. Examples of such a power source include thin film 3D micro batteries. Such power sources are available from companies such as GreatbatchMedical which produces design per specification batteries, or Fullriver® which produces embedded ultra-thin printable batteries. Thin film 3D microbatteries, as developed by Tel-Aviv University, are also a possible power source that can be used with the disclosed technique. As such, the power source of ISSHD 100 can be recharged without having to remove ISSHD 100 from the patient. The power source of ISSHD 100 may thus enable ISSHD 100 to exhibit a long lifetime of usage. In addition, ISSHD 100 is cost effective as compared to prior art ICDs as explained above, due to it being manufactured and packaged as a single component and to its relatively simple implantation and removal procedures which can be executed by a single physician using only local anesthetics.

ISSHD 100 may be manufactured in various predefined sizes. For example, ISSHD 100 may be manufactured at three predefined thicknesses such that it can be positioned subcutaneously in an aesthetic manner depending on the body size and composition of the patient. As another example, ISSHD 100 may also be manufactured at five predefined lengths such that it can be positioned properly around the heart of the patient to give effective electrical shocks to the heart depending on the size and build of the patient.

As shown below in FIG. 2B, the elements of ISSHD 100 are all included within a single integrated structure. As such, ISSHD 100 does not include a can as in prior art ICDs. Due to the size and shape of ISSHD 100, there are no disfiguring bumps on the chest of a patient when ISSHD 100 is inserted and positioned within a patient. This is unlike prior art ICDs in which the can may protrude from under the skin, causing a disfiguring bump on the chest or under the ribs of a patient. In addition, ISSHD 100 also does not include any connectors to separate electrical leads. The electrical leads of ISSHD 100 as well as any connectors coupling the electrical leads to the electronics are all included within ISSHD 100. In order to provide electric shocks to the heart, ends 102A and 102B need to be positioned across the heart. As such, ISSHD 100 has an elongated flexible cylindrical shape which enables an increase in the distance between ends 102A and 102B and also enables ISSHD 100 to be positioned in various configurations around the heart. These configurations are shown below and explained in greater detail in FIGS. 4A-4F. It is noted that in another embodiment of the disclosed technique, ISSHD 100 is coated with PTFE (polytetrafluoroethylene, known commercially as Teflon®) at the time of manufacture, giving the outer surface of ISSHD 100 a smooth and slippery feel. ISSHD 100 may thus be easily inserted and removed (if necessary) with a decreased concern of ISSHD 100 adhering to the muscle tissue or soft tissue around the heart as the body of the patient heals from the injection process of positioning ISSHD 100 around the heart. Furthermore, ISSHD 100 may have a variety of string-like shapes, as described above and as shown in some examples below in FIG. 8.

Reference is now made to FIG. 2B, which is a schematic perspective cutaway illustration of the injectable subcutaneous string heart device of FIG. 2A, generally 120, constructed and operative in accordance with another embodiment of the disclosed technique. As shown, ISSHD 120 includes an inner cylinder 104, an outer cylinder 110 and an electrical lead 106. A hollow 112 is shown where a power source (not shown), at least one capacitor (not shown) and electronics (not shown) can be positioned along the length of ISSHD 120. In one embodiment of the disclosed technique (not shown in FIG. 2B), electrical lead 106 can also be positioned within hollow 112. However, in FIG. 2B, electrical lead 106 is shown as being a part of outer cylinder 110. FIG. 2B shows an end of ISSHD 120. Electrical lead 106 is substantially an electrode for measuring electrical activity of the heart (not shown) of a patient (not shown), providing the measured electrical activity to electronics and for delivering electric shocks to the heart of the patient. In this respect, electrical lead 106 is both passive (as a measuring element) and active (as an electric shock providing element). In the embodiment shown in FIG. 2B, electrical lead 106 has a double helix configuration, where one helix is formed by a first spring 108A and the other helix is formed by a second spring 108B. The double helix configuration is explained in greater detail below in FIG. 3A. Electrical lead 106 does not extend the entire length of ISSHD 120. Electrical lead 106 is coupled with the electronics via cables (not shown) or connectors (not shown), which are also integrated into hollow 112.

Electrical lead 106 is positioned at an end (not labeled) of ISSHD 120. Another electrical lead (not shown) is positioned at the other end of ISSHD 120. As shown, the cross-section of ISSHD 120 is circular and not flat, thus increasing the flexibility of ISSHD 120. This enables ISSHD 120 to be inserted in a patient subcutaneously and also enables ISSHD 120 to be inserted into a patient without needing to keep the angular position of ISSHD 120 steady and constant as it is inserted into the patient. In addition, the flexible shape of ISSHD 120 can be adapted to fit any longitudinal shape and does not require any modification to be inserted into individuals having different body shapes and sizes. It is also noted that one end (not labeled) of ISSHD 120 may be closed. For example, inner cylinder 104 may be hollow yet one of its ends may be closed such that a guidewire or medical stylet can be pushed through inner cylinder 104 and then used to push ISSHD 120 into position inside a patient. In another embodiment, outer cylinder 110 may have one of its ends closed such that a guidewire or medical stylet can be pushed through hollow 112 and the used to push ISSHD 120 into position inside a patient. In a further embodiment, outer cylinder 110 may be closed on both ends, with inner cylinder 110 being hollow and being open on only one end.

As shown above in FIG. 2B, the ISSHD of the disclosed technique has a circular and conformal shape. As such, the electrical leads of the disclosed technique, which are substantially electrodes, also require a circular and conformal shape. This is unlike the prior art in which electrodes may have a flat shape. In addition, the conformal shape of the electrical leads of the disclosed technique obviates the need for the electrical leads to be at a specific angle. In addition, the electrical leads of the disclosed technique include two elements in each electrical lead. Two configurations of the electrical leads of the disclosed technique are shown below in FIGS. 3A and 3B which conform to these characteristics.

Figure 3A:
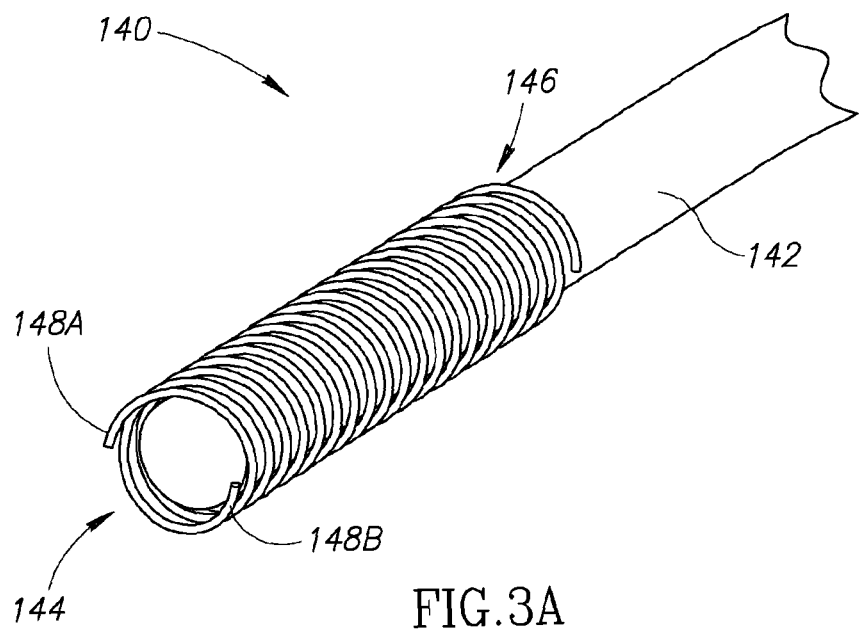
FIG. 3A is a schematic illustration of an electrode of the injectable subcutaneous string heart device of FIG. 2B, exhibiting a double helix configuration, constructed and operative in accordance with a further embodiment of the disclosed technique.

Reference is now made to FIG. 3A, which is a schematic illustration of an electrode of the injectable subcutaneous string heart device of FIG. 2B, exhibiting a double helix configuration, generally referenced 140, constructed and operative in accordance with a further embodiment of the disclosed technique. As shown, ISSHD 140 includes an inner cylinder 142 and an electrical lead 146. An outer cylinder (not shown) surrounds inner cylinder 142 and electrical lead 146. As mentioned above, in one embodiment, electrical lead 146 may form a part of the outer cylinder. The outer cylinder is not drawn in FIG. 3A to properly illustrate the configuration of electrical lead 146. ISSHD 140 has two ends, one end 144 as shown in FIG. 3A and another end, which is not shown. The other end is substantially identical to end 144 as shown in FIG. 3A. Electrical lead 146 includes two elements in the form of a helix or spring, a first element 148A and a second element 148B. Each one of first element 148A and second element 148B can be made from a metal or a conductive material such as platinum, iridium, gold, stainless steel and the like. Together, first element 148A and second element 148B form a double helix configuration where each helix is separated and isolated from the other. As shown, first element 148A and second element 148B are not in contact with one another even though they are in close proximity to one another.

Each one of first element 148A and second element 148B can be used passively to monitor and sense electrical activity of a heart (not shown) and provide the sensed and monitored electrical activity to electronics (not shown) positioned further along ISSHD 140. Each one of first element 148A and second element 148B can also be used actively to provide electric shocks to the heart. In one embodiment, one element is used to passively monitor and sense electrical activity of the heart whereas the other element is used to actively provide electric shocks to the heart. In this respect, this embodiment enables sensing and monitoring of the electrical activity of the heart to occur simultaneously as electric shocks are provided to the heart. There is therefore no need to perform any time sharing of a single electrical lead for both sensing and monitoring the electrical activity of the heart and also for providing electric shocks to the heart. In this embodiment, sensing and monitoring of the electrical activity of the heart can also occur after electric shocks are provided to the heart. In another embodiment, only one element, such as first element 148A, is used to both passively sense electrical activity of the heart and also to actively provide electric shocks to the heart. Usually the sensing of electrical activity of the heart and the providing of electric shocks to the heart do not occur simultaneously. Besides regular monitoring of the electrical activity of the heart, sensing of the electrical activity of the heart may occur after an electric shock was provided to the heart in order to measure if the provided electric shock was sufficient to defibrillate the heart, as in the case of cardiac arrest, or to restore the regular beating rhythm of the heart, as in the case of an arrhythmia. According to the disclosed technique, a redundant second element for both sensing the electrical activity of the heart and for providing electric shocks to the heart is provided in case the first element ceases to function. In many prior art ICDs and pacemakers, the element which monitors electrical activity or which provides electric shocks or impulses to the heart may break, fracture or malfunction. Such a break, fracture or malfunction may not be recognized by a patient (not shown). In addition, the patient may also exhibit an irregularity in his heartbeat requiring an ICD or pacemaker to work. Due to the break, fracture or malfunction, the ICD or pacemaker may not work and the patient may suffer irreversible damage or possibly death due to the malfunctioning of the ICD or pacemaker placed inside him. According to the disclosed technique, the probability of such a scenario is reduced as two separate independent elements are provided in each electrical lead such that if one element breaks, fractures or malfunctions, the other element can be used in its place. The electronics of the disclosed technique may be provided with the ability to monitor the functioning of the two elements in each electrical lead for malfunctions. The electronics may monitor the integrity of each of the two elements in each electrical lead for fractures, breaks or unusual electrical characteristics. For example, the electronics may monitor each of the two elements for an electrical impedance which is characteristically higher or lower than a predefined range of normal operational electrical impedances. If one element in an electrical lead malfunctions or breaks, the electronics can automatically switch the element currently being used to the other element such that the ISSHD of the disclosed technique functions properly and will not be disabled in the event that one element malfunctions or fractures. Such is the case with existing known implantable devices in which such devices may cease to function due to a break, fracture or malfunction in one of the electrical elements. In the case of a malfunction or break in one of the elements in an electrical lead, the ISSHD may alert the patient to the break, failure or malfunction by delivering a low energy electric shock (even lower than the voltages used for pacing the heart) at a pre-programmed time every day for a pre-determined amount of time. In addition, the ISSHD may alert the patient to the break, failure or malfunction via a handheld transceiver, as described below. In addition, the electronics may store a message or provide a message to a medical practitioner, such as a cardiologist, notifying them that one element of the ISSHD implanted in the patient has malfunctioned or is broken. The message may be provided to the medical practitioner when the patient comes in for a routine check-up on the functioning of their ISSHD and messages stored in the electronics of the ISSHD are retrieved wirelessly by the medical practitioner. The ISSHD of the disclosed technique can thus be easy checked by the patient and by the medical practitioner, making the ISSHD a device which is easy to maintain. For example, the ISSHD may include a small transceiving element, such as a Bluetooth element (not shown), enabling communication between the ISSHD and an external communication terminal. The external communication terminal may be a Bluetooth enabled device, such as a smartphone or a tablet computer. From the patient's point of view, the ISSHD may be able to transmit a status report about the function of their device to the external communication terminal, such that the patient can easily maintain their device and be aware of when they should visit their medical practitioner for problems with the device. The status report transmitted to the patient may indicate that one of the elements in one of the electrical leads has malfunctioned or is not working properly. From the medical practitioner's point of view, the ISSHD could be reprogrammed via the external communication terminal, besides also providing diagnostic information about the functioning of the ISSHD to the medical practitioner. The communication protocol used for the transceiving element must be secure in order to avoid any involuntary changes to the programming of the ISSHD of the disclosed technique. The ISSHD of the disclosed technique can provide a patient, in addition to a medical practitioner, the ability to perform a simple check on the status of the ISSHD from home or on the road with a small pocket-sized transceiver. Immediate reassurance can thus be provided to the patient that the ISSHD is functioning normally. This will greatly decrease the significant follow-up currently now required to check on the status of existing implantable transvenous ICDs.

Figure 3B:
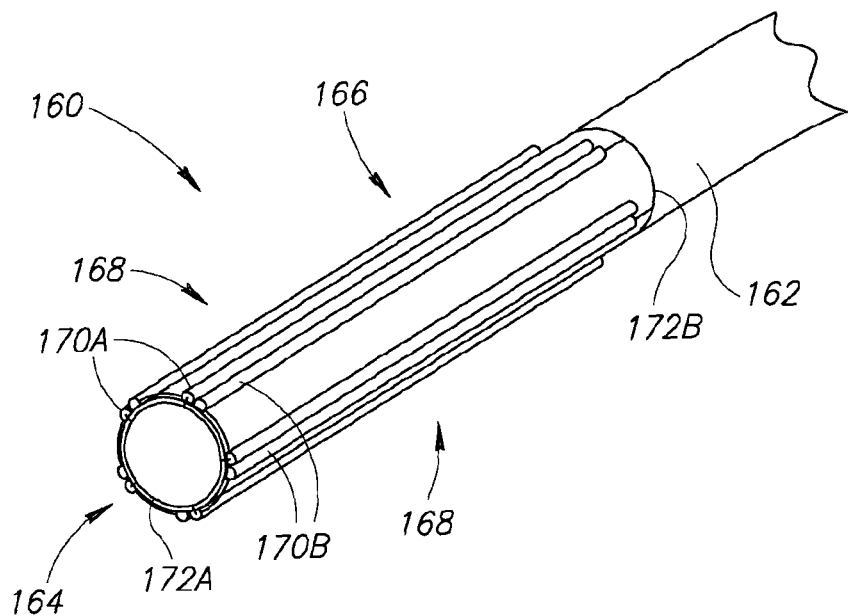
FIG. 3B is a schematic illustration of an electrode of the injectable subcutaneous string heart device of FIG. 2B, exhibiting a linear pairs configuration, constructed and operative in accordance with another embodiment of the disclosed technique.

Reference is now made to FIG. 3B, which is a schematic illustration of an electrode of the injectable subcutaneous string heart device of FIG. 2B, exhibiting a linear pairs configuration, generally referenced 160, constructed and operative in accordance with another embodiment of the disclosed technique. As shown, ISSHD 160 includes an inner cylinder 162 and an electrical lead 166. An outer cylinder (not shown) surrounds inner cylinder 162 and electrical lead 166. In another embodiment, electrical lead 162 may form part of the outer cylinder. The outer cylinder is not drawn in FIG. 3B to properly illustrate the configuration of electrical lead 166. ISSHD 160 has two ends, one end 164 as shown in FIG. 3B and another end, which is not shown. The other end is substantially identical to end 164 as shown in FIG. 3B. Electrical lead 166 includes a plurality of pairs of linear conductors 168. Each pair of linear conductors 168 includes a first conductor 170A and a second conductor 170B, which are parallel to each other. Each pair of linear conductors 168 can be made from a metal or from other conductive materials such as platinum, iridium, gold, stainless steel and the like. Together, the plurality of pairs of linear conductors 168 forms a linear pairs configuration of electrical lead 166. Plurality of pairs of linear conductors 168 forms a circular shape around end 164. First conductor 170A and second conductor 170B in a pair of linear conductors are not coupled with one another. However, each first conductor of each pair of linear conductors 168 is coupled with one another and each second conductor of each pair of linear conductors 168 is coupled with one another. Thus the first conductors of plurality of pairs of linear conductors 168 form a first coupled spiral conductor (not labeled) around end 164 and the second conductors of plurality of pairs of linear conductors 168 form a second coupled spiral conductor (not labeled) around end 164. As shown, each first conductor 170A is electrically coupled to its neighboring first conductors 170A by a wire 172A, thus forming a first coupled spiral conductor. Each second conductor 170B is electrically coupled to its neighboring second conductors 170B by a wire 172B, thus forming a second coupled spiral conductor.

Like in ISSHD 140 (FIG. 3A), the electrical leads of ISSHD 160 can be used actively and passively simultaneously for sensing and monitoring electrical activity of the heart as well as providing electric shocks to the heart if required. For example, first conductor 170A of each pair of linear conductors 168 may be coupled together and function as a passive electrode whereas second conductor 170B of each pair of linear conductors 168 may also be coupled together and function as an active electrode. Alternatively, one conductor in each pair of linear conductors 168 may function as both an active and passive first electrode, with the other conductor in each pair of linear conductors 168 functioning as a redundant second electrode to be used in case the first electrode breaks, fractures or malfunctions, as was explained above in FIG. 3A.

The electrical leads or electrodes of the ISSHD of the disclosed technique substantially conduct electricity between themselves. Therefore, the electrodes do not need to physically touch the heart to administer an electric shock to the heart, but they must be properly positioned such that any current or voltage traveling from one electrode to the other also passes through the heart. In general, for defibrillation, the current and voltage must pass through the ventricles of the heart in order for the electric shock to be effective. For pacing, the same is true, although the voltages administered need to be substantially lower. Therefore, there is no need for the electrical leads of the ISSHD of the disclosed technique to actually touch the heart or its inner parts to effect defibrillation and/or pacing. According to the disclosed technique, three example implantation or implanting configurations are shown of the ISSHD of the disclosed technique in FIGS. 4A-4F. In each configuration, one electrode is positioned in proximity to one ventricle of the heart whereas the other electrode is positioned in proximity to the other ventricle of the heart such that electricity passing from one electrode to the other passes through both ventricles of the heart.

Reference is now made to FIGS. 4A and 4B, which are schematic illustrations of a first implanting configuration of the injectable subcutaneous string heart device of FIG. 2A, generally referenced 200, constructed and operative in accordance with a further embodiment of the disclosed technique. FIG. 4A is a frontal perspective view showing the first implanting configuration, whereas FIG. 4B shows the same implanting configuration except from a side perspective view. Reference numbers between FIGS. 4A and 4B are thus the same. In FIG. 4A, a patient 202 with a heart 204 is shown. Heart 204 includes a right ventricle 210A and a left ventricle 210B. An ISSHD 206 is positioned over heart 204 such that one electrode 208A is positioned to the right of the sternum (not shown) and that the other electrode 208B is positioned to the left of the sternum. The sternum is the flat bone which lies in the middle front part of the ribcage and is posterior to heart 204. In FIG. 4B, it can be seen that ISSHD 206 is positioned in a quasilinear configuration over heart 204, as only electrode 208B is viewable in patient 202 from a side perspective view and ISSHD 206 appears as a point. ISSHD 206 substantially follows the curve of the chest of the patient in its configuration.

Reference is now made to FIGS. 4C and 4D, which are schematic illustrations of a second implanting configuration of the injectable subcutaneous string heart device of FIG. 2A, generally referenced 220, constructed and operative in accordance with another embodiment of the disclosed technique. FIG. 4C is a frontal perspective view showing the second implanting configuration, whereas FIG. 4D shows the same implanting configuration except from a side perspective view. Reference numbers between FIGS. 4C and 4D are thus the same. In FIG. 4C, a patient 222 with a heart 224 is shown. Heart 224 includes a right ventricle 230A and a left ventricle 230B. An ISSHD 226 is positioned over heart 224 such that one electrode 228A is positioned to the right of the sternum (not shown) and that the other electrode 228B is positioned below the left side of the sternum. As shown, ISSHD 226 is positioned in an L-configuration around heart 224. In FIG. 4D, it can be seen that ISSHD 226 is positioned in an L-configuration over heart 224, as only electrode 228B is viewable in patient 222 from a side perspective view and ISSHD 226 appears as a line.

Figures 4E, 4F:
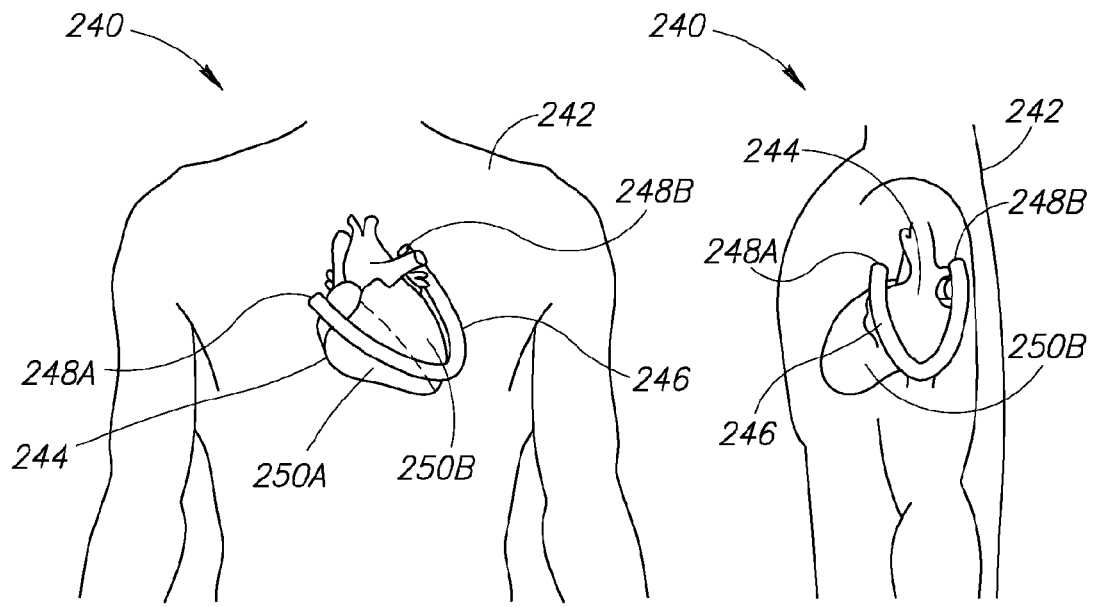
FIGS. 4E and 4F are schematic illustrations of a third implanting configuration of the injectable subcutaneous string heart device of FIG. 2A, constructed and operative in accordance with a further embodiment of the disclosed technique.

Reference is now made to FIGS. 4E and 4F, which are schematic illustrations of a third implanting configuration of the injectable subcutaneous string heart device of FIG. 2A, generally referenced 240, constructed and operative in accordance with a further embodiment of the disclosed technique. FIG. 4E is a frontal perspective view showing the third implanting configuration, whereas FIG. 4F shows the same implanting configuration except from a side perspective view. Reference numbers between FIGS. 4E and 4F are thus the same. In FIG. 4E, a patient 242 with a heart 244 is shown. Heart 244 includes a right ventricle 250A and a left ventricle 250B. An ISSHD 246 is positioned over heart 244 such that one electrode 248A is positioned above the sternum (not shown) and that the other electrode 248B is positioned on the left side of patient 242, above the ribs. As shown, ISSHD 246 is positioned in a U-configuration around heart 224. In FIG. 4F, it can be seen that ISSHD 246 is positioned in a U-configuration around heart 244, with electrode 248A being viewable as being in front of heart 244 and electrode 248B being viewable as being behind heart 244. In addition, ISSHD 246 appears as a quasi half-circle or quasi half-ellipse. It is noted that other configurations of the ISSHD of the disclosed technique around the heart of a patient are possible and are within the knowledge of the worker skilled in the art. For example, the ISSHD may be implanted from a lateral side of the patient, or from the back of the patient, and brought around to the front side of the patient ending at their sternum. It is noted that this configuration may provide a more cosmetically pleasing result to the patient as there will be no incisions made at the front of the chest or near the midline.

Figure 5:
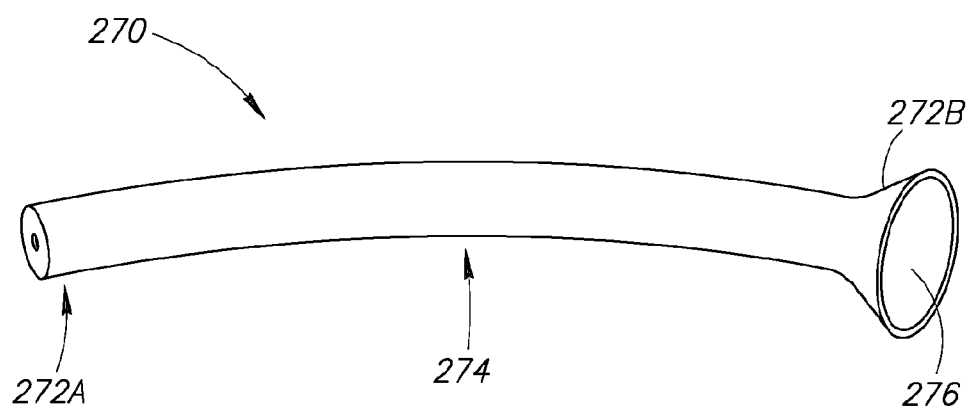
FIG. 5 is a schematic perspective illustration of another injectable subcutaneous string heart device, constructed and operative in accordance with another embodiment of the disclosed technique.

Reference is now made to FIG. 5, which is a schematic perspective illustration of another injectable subcutaneous string heart device, generally referenced 270, constructed and operative in accordance with another embodiment of the disclosed technique. ISSHD 270 is substantially similar to ISSHD 100 (FIG. 2A). ISSHD 270 includes two ends, an end 272A and an end 272B. Each end may include an electrical lead (not shown). The space of ISSHD 270 between ends 272A and 272B, shown by an arrow 274, may be used for positioning other elements of ISSHD 270, such as a power source (not shown) and electronics (not shown). In ISSHD 100, the space was also used for positioning at least one capacitor or a plurality of capacitors along the length of ISSHD 100. In ISSHD 270, end 272B has an enlarged space 276. Enlarged space 276 has a conical shape. Enlarged space 276 can be used for specifically housing the at least one capacitor or the plurality of capacitors, instead of having to place them in space 274.

Figure 6A:
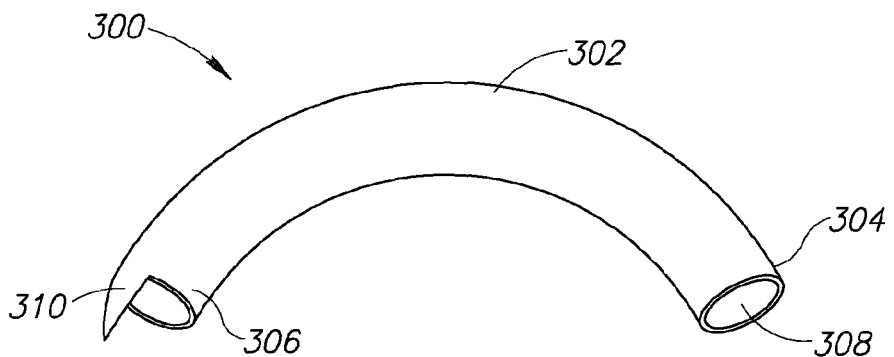
FIG. 6A is a schematic illustration of a first injection device for inserting the injectable subcutaneous string heart device of FIG. 2A in a patient, constructed and operative in accordance with a further embodiment of the disclosed technique.

According to the disclosed technique, the ISSHD of the disclosed technique, such as ISSHD 100 (FIG. 2A) or ISSHD 270 (FIG. 5) can be inserted and implanted in a patient with minimal invasion. In addition, the ISSHD of the disclosed technique can be easily implanted in a patient. An injection device, such as a semi-flexible trocar, can be used for injecting the ISSHD of the disclosed technique subcutaneously. As such, only a small incision needs to be made in a patient (not shown) for inserting the ISSHD subcutaneously in a position around the heart (not shown) of the patient. Different embodiments of the injection device are shown below in FIGS. 6A-6C. Reference is now made to FIG. 6A, which is a schematic illustration of a first injection device for inserting the injectable subcutaneous string heart device of FIG. 2A in a patient, generally referenced 300, constructed and operative in accordance with a further embodiment of the disclosed technique. First injection device 300 may be a semi-flexible trocar. First injection device 300 has an elongated cylindrical shape 302, having a proximal end 304 and a distal end 306. Proximal end 304 is flat whereas distal end 306 includes a sharp tip 310 for inserting first injection device 300 subcutaneously. First injection device 300 is hollow, as shown by an arrow 308 and has a diameter which is larger than a diameter of ISSHD 100 (FIG. 2A), such that ISSHD 100 can be maneuvered through hollow 308 of first injection device 300. First injection device 300 may be made from a semi-flexible material such as plastic, silicon, titanium and the like. First injection device 300 may measure, for example, between 30 to 50 centimeters in length and between 5-10 millimeters in diameter.

As an example of how first injection device 300 is used to insert ISSHD 100 in a patient, the following description is provided assuming first injection device 300 is used to insert ISSHD 100 in an L-configuration in a patient, as shown above in FIGS. 4C and 4D. A worker skilled in the art would easily be able to modify the method of inserting first injection device 300 described below for inserting first injection device 300 in any desired configuration in a patient provided the two electrical leads (not show) of ISSHD 100 are properly positioned, as described above in FIGS. 4A-4F. An incision is made in a patient (not shown) just below the left side of his or her ribs. Using sharp tip 310, first injection device 300 is inserted subcutaneously through the incision. Due to the semi-flexible material it is fabricated from, first injection device 300 can be pushed along the ribcage of the patient, below the chest muscles, and then along the sternum until sharp tip 310 reaches the upper portion of the sternum. In one embodiment of the disclosed technique, sharp tip 310 remains within the body of the patient. In another embodiment of the disclosed technique, sharp tip 310 is pushed through the skin such that it exits the body of the patient at a distal point above the sternum. In either embodiment, first injection device 300 is now in place for the insertion of ISSHD 100 within the patient. In another embodiment of the disclosed technique, a stiff guidewire (not shown) is initially used to pave the way for first injection device 300. Once the guidewire is in place, first injection device 300 is pushed over the guidewire toward its position within the body. The guidewire is then pulled out and ISSHD 100 can then be inserted into first injection device 300.

As ISSHD 100 has a diameter smaller than the diameter of first injection device 300, ISSHD 100 can be threaded through hollow 308 until it is positioned in its desired location. In one embodiment of the disclosed technique, the inner cylinder (not shown) of ISSHD 100 has a hollow (not shown). A stiff guidewire or a tool shaped like a stiletto or stylet may be inserted in the hollow in the inner cylinder for maneuvering ISSHD 100 to its final position. It is noted that in this embodiment, the inner cylinder may be closed at its distal end, which is initially inserted into a patient, such that an end of the guidewire, stiletto or stylet actually pushes the end of ISSHD 100 into the patient. In an alternative embodiment, the guidewire, stiletto or stylet may be inserted into the space between the inner cylinder and the outer cylinder (not shown) of ISSHD 100. In this embodiment, the outer cylinder is closed at its distal end, such that the guidewire, stiletto or stylet actually pushes the end of ISSHD 100 into the patient. In another embodiment of the disclosed technique, an end of ISSHD 100, such as end 102A (FIG. 2A) may include a ferromagnetic element (not shown) or strong rare earth magnetic bead. A strong external magnet field may then be used to maneuver ISSHD 100 within first injection device 300 and to temporarily anchor a distal end (not labeled) of ISSHD 100 while ISSHD 100 is completely inserted inside the patient. The strong external magnetic field may also be used while first injection device 300 is removed from the patient, thus keeping ISSHD 100 stationary in its position. The strong magnetic field may be generated by a magnet or an electromagnetic. In a further embodiment, when sharp tip 310 exits the body of the patient at a distal point above the sternum, a wire (not shown) may be coupled with the distal end of ISSHD 100. The wire is then threaded through first injection device 300 such that it exits the patient at the distal point above the sternum. The wire can then be used to pull ISSHD 100 through first injection device 300. Since ISSHD 100 is flexible in nature, it does not need to be pre-shaped before it is inserted into the patient. ISSHD 100 thus takes the shape of the configuration in which it is inserted into the patient.

Once ISSHD 100 has been fully inserted inside the body of the patient, first injection device 300 is removed from the patient. If sharp tip 310 exited the patient at a distal point above the sternum, then distal end 306 can simply be pulled through that distal point, thereby removing first injection device 300 from the patient. The original incision and the distal point are then sutured up. If sharp tip 310 did not exit the patient, then proximal end 304 is pulled, thereby removing first injection device 300 from the patient via the original incision made to first insert first injection device 300 into the patient. The original incision is then sutured up. Once first injection device 300 is removed, since ISSHD 100 sits within the muscle tissue surrounding the heart, ISSHD 100 will substantially remain stationary in its position within the patient. As such, there is no need to anchor ISSHD 100 to anything within the patient. According to another embodiment of the disclosed technique, the distal end of ISSHD 100, such as end 102A, may include a corkscrew element (not shown). Once ISSHD 100 is deployed within the patient, ISSHD 100 is turned, thus turning the corkscrew element and inserting it into the muscle tissue surrounding the sternum, the ribs or both. The distal end of ISSHD 100 thus becomes anchored and secured within the patient according to this embodiment. According to a further embodiment of the disclosed technique, the distal end of ISSHD 100 may be held stationary via an electromagnetic, as described above, as first injection device 300 is removed, thus not dislodging ISSHD 100 as first injection device 300 is removed from the patient. According to another embodiment of the disclosed technique, first injection device 300 and ISSHD 100 can be coated with an inert biodegradable material such as mannitol before either one is inserted inside the patient. The inert biodegradable material, such as mannitol, substantially acts as a glue, thus keeping ISSHD 100 and first injection device 300 coupled together while they are inserted into the patient. Once inserted, the medical practitioner may wait a few minutes, as the inert biodegradable material begins to melt. After a few minutes have elapsed and the inert biodegradable material has melted, first injection device 300 can be easily removed without dislodging ISSHD 100. In an alternative embodiment of the disclosed technique, a clip or fastener can be used to couple ISSHD 100 and first injection device 300 together while they are inserted into the patient. The clip or fastener may include a release mechanism which can disconnect the two elements. Thus, once ISSHD 100 is in place, first injection device 300 can be released from ISSHD 100 and then removed from the patient, leaving ISSHD 100 in place. According to a further embodiment of the disclosed technique, two incisions are made in a patient, a first incision near the position in the patient where a proximal end of ISSHD 100 will remain once inserted and a second incision near the position in the patient where a distal end of ISSHD 100 will remain once inserted. Each incision is no more than 1 centimeter in length. In this embodiment, first injection device 300 is inserted through the first incision and brought to a position near the second incision. A rubber or nylon tube (not shown) is then inserted into first injection device 300 via the second incision and is threaded through first injection device 300 until its distal end exits the patient at the first incision. ISSHD 100 is then attached to the tube which is pulled through first injection device 300, thereby pulling ISSHD 100 through first injection device 300 and into its desired position. Once ISSHD 100 is in the desired position, first injection device 300 is removed while leaving ISSHD 100 in place. This can be executed by using strong magnets and a strong magnetic field to hold ISSHD 100 in place while first injection device 300 is removed, as described above. A suture can be placed at both the first and second incision sites, thus anchoring ISSHD 100 in place.

Figure 6B:
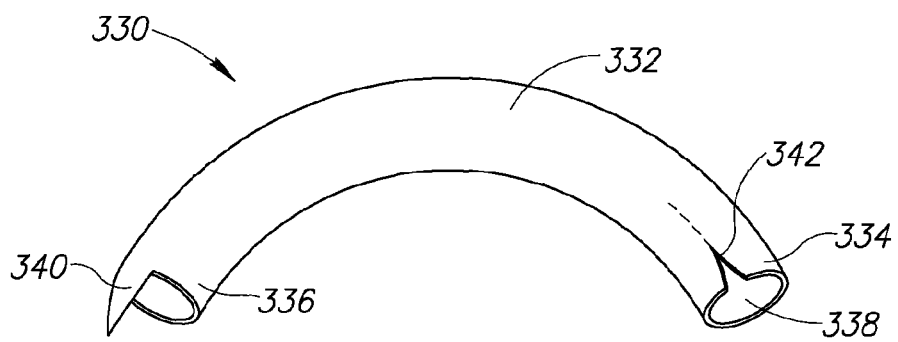
FIG. 6B is a schematic illustration of a second injection device for inserting the injectable subcutaneous string heart device of FIG. 5 in a patient, constructed and operative in accordance with another embodiment of the disclosed technique.

Reference is now made to FIG. 6B, which is a schematic illustration of a second injection device for inserting the injectable subcutaneous string heart device of FIG. 5 in a patient, generally referenced 330, constructed and operative in accordance with another embodiment of the disclosed technique. Second injection device 330 may be a trocar. Second injection device 330 has an elongated cylindrical shape 332, having a proximal end 334 and a distal end 336. Proximal end 334 is flat whereas distal end 336 includes a sharp tip 340 for inserting second injection device 330 subcutaneously. Second injection device 330 is hollow, as shown by an arrow 338 and has a diameter which is larger than a diameter of ISSHD 270 (FIG. 5), such that ISSHD 270 can be maneuvered through hollow 338 of second injection device 330. However, enlarged space 276 (FIG. 5) has a diameter which is larger than the diameter of second injection device 330. Second injection device 330 is substantially similar to first injection device 300 (FIG. 6A) except that second injection device 330 is specifically designed to accommodate ISSHD 270 which has an enlarged space at its proximal end. Proximal end 334 may include a pre-cut portion 342 for accommodating enlarged space 276. Second injection device 330 is used in a manner similar to first injection device 300 as described above in FIG. 6A with a slight modification. ISSHD 270 is inserted through second injection device 330 once it is properly positioned. However, enlarged space 276 is not inserted through second injection device 330. Once all of ISSHD 270 is inserted through second injection device 330 into a patient (not shown), except for enlarged space 276, second injection device 330 is removed from the patient. Second injection device 330 can be removed by pulling it through a distal point above the sternum, as described above in FIG. 6A, if sharp tip 340 exits the body of the patient. If sharp tip 340 does not exit the body of the patient, proximal end 334 may need to be cut, as shown by pre-cut portion 342, such that second injection device 330 can be pulled over enlarged space 276. Pre-cut portion 342 may be pre-cut before second injection device 330 is inserted into a patient or it may be cut only once second injection device 330 is to be removed from the patient. Once second injection device 330 has been removed from the patient, enlarged space 276 is then inserted into the patient and any incisions made during the implantation process are sutured up.

Figure 6C:
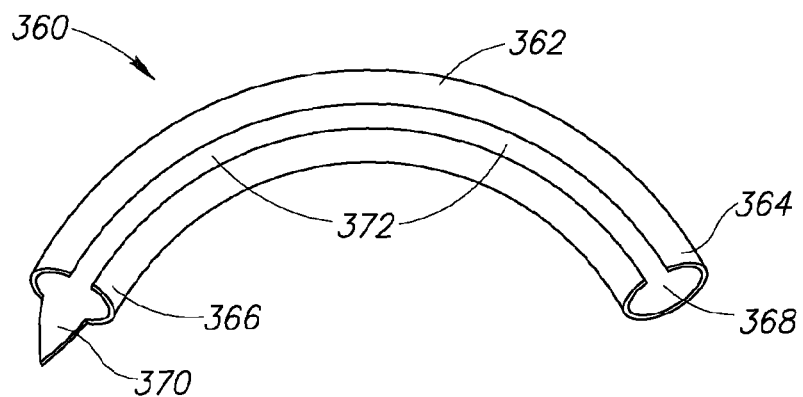
FIG. 6C is a schematic illustration of a third injection device for inserting the injectable subcutaneous string heart device of FIG. 5 in a patient, constructed and operative in accordance with a further embodiment of the disclosed technique.

Reference is now made to FIG. 6C, which is a schematic illustration of a third injection device for inserting the injectable subcutaneous string heart device of FIG. 5 in a patient, generally referenced 360, constructed and operative in accordance with a further embodiment of the disclosed technique. Third injection device 360 may be a trocar. Third injection device 360 has an elongated cylindrical shape 362, having a proximal end 364 and a distal end 366. Proximal end 364 is flat whereas distal end 366 includes a sharp tip 370 for inserting third injection device 360 subcutaneously. Third injection device 360 is hollow, as shown by an arrow 368 and has a diameter which is larger than a diameter of ISSHD 270 (FIG. 5), such that ISSHD 270 can be maneuvered through hollow 368 of third injection device 360. Third injection device 360 is substantially similar to second injection device 330 (FIG. 6B). Like second injection device 330, third injection device is specifically designed to accommodate ISSHD 270 which has an enlarged space at its proximal end. Third injection device 360 includes a gap 372, running along its length, as shown in FIG. 6C. Gap 372 enables third injection device 360 to accommodate enlarged space 276 (FIG. 5) of ISSHD 270 without having to cut a portion of third injection device 360, either prior to or after the insertion of the injection device in the body of a patient, as in the case of second injection device 330. Third injection device 360 is used in a manner similar to second injection device 330 as described above in FIG. 6B. If sharp tip 370 does not exit the body of the patient, third injection device 360 can be pulled over enlarged space 276 because of gap 372.

The ISSHD of the disclosed technique can be easily removed in a manner similar to how it was inserted, as described above in FIGS. 6A-6C. For example, the original incision made on the left side of the body of the patient below the ribcage can be opened up and the proximal end of the ISSHD can be pulled, thereby removing the ISSHD from the patient. If the distal end of the ISSHD includes a corkscrew, then the ISSHD can be rotated counterclockwise, thus releasing the corkscrew from the muscle tissue around the sternum and/or ribs. In another embodiment of the disclosed technique, the corkscrew of the ISSHD can rotate independently of the ISSHD. In such an embodiment, a stiletto can be inserted through the hollow inner cylinder of the ISSHD and used to rotate the corkscrew counterclockwise, thereby releasing the ISSHD from the muscle tissue it is coupled with. Mechanisms for an independent rotatable corkscrew inserted inside an ICD are known in the art. The ISSHD can then be gently pulled from the body of the patient. According to another embodiment of the disclosed technique, if the ISSHD of the disclosed technique needs to be removed from a patient and another ISSHD is to be inserted into the patient, then a guidewire may be used to both remove the old ISSHD and insert a new ISSHD. For example, once the original incision is opened up, the proximal end of the ISSHD may be removed enough to insert a guidewire through the hollow of the ISSHD. The guidewire can then be maneuvered to the distal end of the ISSHD. The ISSHD can then be removed using the guidewire as a guiding surface. Once removed, a new ISSHD can be reinserted into the patient over the guidewire which is currently properly positioned inside the patient for the insertion of the new ISSHD. The new ISSHD will then be positioned in approximately the same position as the old ISSHD was positioned in. According to this embodiment, there is no need for another injection device to be used to insert the new ISSHD as the guidewire used to remove the old ISSHD obviates the need for an injection device. An old ISSHD may need to be replaced with a new ISSHD since it may need to be recharged, it may have malfunctioned, the power source may be dead or an upgraded version of the ISSHD is available.

Figure 7:
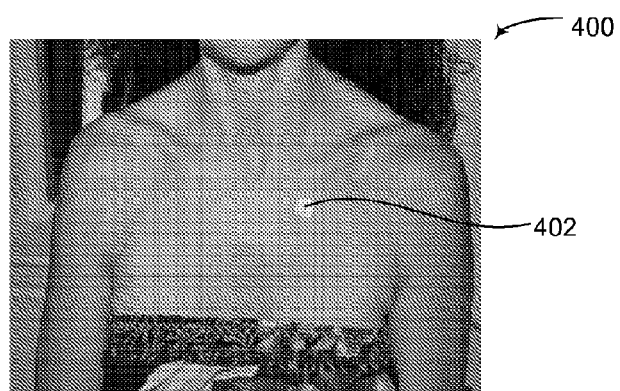
FIG. 7 is a photo showing an insertion mark of the injection devices of FIGS. 6A-6C in a patient, constructed and operative in accordance with another embodiment of the disclosed technique.

Reference is now made to FIG. 7, which is a photo showing an insertion mark of the injection devices of FIGS. 6A-6C in a patient, generally referenced 400, constructed and operative in accordance with another embodiment of the disclosed technique. As shown, once the ISSHD of the disclosed technique is implanted under the skin of a patient 402, the ISSHD is not noticeable. In addition, if the injection device for inserting the ISSHD was exited via a distal point above the sternum, only a small mark 404 remains visible on the chest of patient 402. The initial incision made in patient 402 may still be visible as well, yet as explained above, such an incision may be made under the ribs such that when patient 402 wears a shirt or dress, the incision will not be visible to onlookers.

With reference back to FIG. 2A, according to the disclosed technique, ISSHD 100 includes electronics which may include elements enabling wireless communication. For example, the electronics may include a radio frequency (herein abbreviated RF) transceiver that can transmit and receive signals. The RF transceiver may be able to transmit and receive wireless signals using the wireless fidelity (herein abbreviated WiFi) communication protocol or the Bluetooth® communication protocol. The RF transceiver enables a medical practitioner, such as a cardiologist, to monitor the function of the ISSHD of the disclosed technique. The Bluetooth® communication protocol may be integrated with a smartphone or a tablet device, such as an iPad®, for remote maintenance and analysis of the ISSHD. The ISSHD may store data relating to various parameters of its use, such as how much power the power source has left, how much charge is being stored on the at least one capacitor, how often is an electric shock administered to the patient via the ISSHD, what kind of electric shocks are being administered to the patient via the ISSHD, the electrical resistance of the electrical leads and the like. The RF transceiver enables the data stored by the ISSHD to be transferred to another medium, such as a personal computer, smartphone, tablet and the like where the medical practitioner can review the data. In addition, the RF transceiver enables the medical practitioner to program and reprogram the ISSHD. As mentioned above, the power source of the ISSHD may be able to be recharged remotely and wirelessly.

As mentioned above, the ISSHD of the disclosed technique can provide various types of electric shocks to the heart of a patient, depending on the sensed arrhythmias of the patient via the electrical leads of the ISSHD. In general, the ISSHD provides electric shocks to treat VF and cardiac arrest and thus functions as an ICD. In addition, the ISSHD may provide electric shocks to treat VT and other arrhythmias. For severe bradycardia, the ISSHD can function as a pacemaker as well. The electric shocks provided when the ISSHD functions as an ICD are in general significantly higher in voltage than the electric shocks and impulses provided when the ISSHD functions as a pacemaker. Due to the position of the ISSHD of the disclosed technique in the soft tissue around the heart, a patient receiving pacing voltages from the ISSHD may notice other muscles in their chest reacting to the pacing voltages, thus causing a thumping-type sensation in the patient. As such, the ISSHD of the disclosed technique may provide pacing voltages only for intermittent emergency-type needs such as extreme bradycardia (i.e., when the heart rate drop below 25 BPM) or post-defibrillation pacing for heart rates less than 45 BPM. As mentioned, the ISSHD of the disclosed technique is programmed to provide pacing voltages only in the case of an emergency, such as when the heartbeat of a patient drops below 30 beats per minute or if the patient suffers cardiac asystole (i.e., flatline). Thus according to the disclosed technique, pacing voltages are provided to the heart of a patient subcutaneously. Pacing voltages can be applied by the ISSHD of the disclosed technique to a patient after the ISSHD has administered a defibrillating electric shock to the heart.

Figure 8:
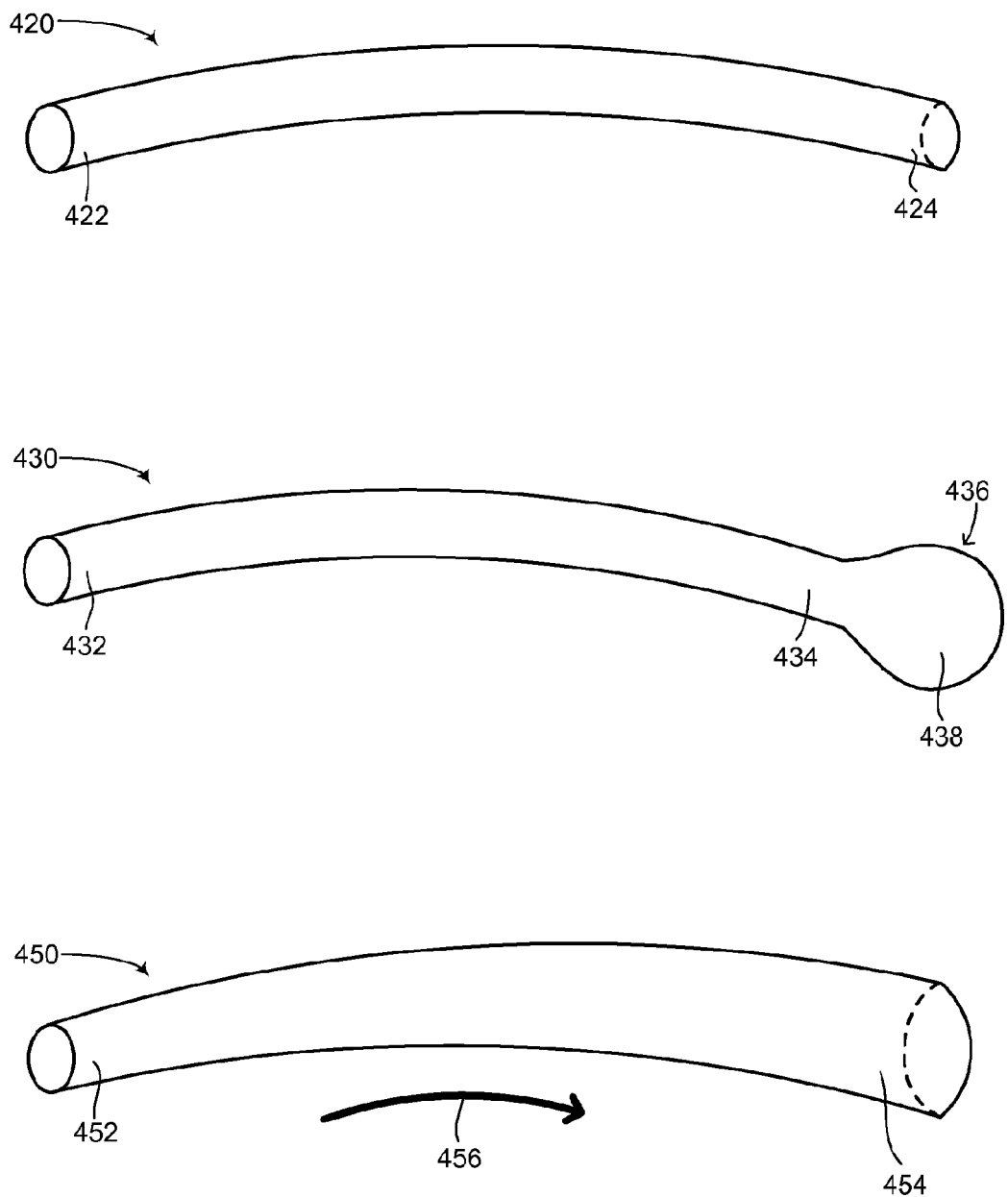
FIG. 8 is a schematic illustration of various possible shapes for an injectable subcutaneous string heart device, constructed and operative in accordance with a further embodiment of the disclosed technique.

Reference is now made to FIG. 8 which is a schematic illustration of various possible shapes for an injectable subcutaneous string heart device, generally referenced 420, 430 and 450 respectively, constructed and operative in accordance with a further embodiment of the disclosed technique. As mentioned above, the ISSHD of the disclosed technique has a general string-like shape. In general, each of the shapes described below is described as having a proximal end and a distal end. These labels however are merely for the purposes of describing the shapes and can easily be switched, such that the proximal end is referred to as the distal end and the distal end is referred to as the proximal end. Shape 420 includes a proximal end 422 and a distal end 424. Shape 420 has a generally cylindrical or tubular shape, characterized by a generally uniform cross-sectional shape and diameter along its length. The cross-sectional shape of shape 420 may have any known curvature. For example, the cross-sectional shape may be a circle, an ellipse or a closed curve. The cross-sectional shape may also be any conic section having an eccentricity ranging from 0 to 1.

Shape 430 includes a proximal end 432 and a distal end 436. Distal end 436 includes two sections, a bulbous end section 438 and an adjacent end structure 434. From proximal end 432 to adjacent end structure 434, shape 430 substantially resembles shape 420, having a generally cylindrical or tubular shape, characterized by a generally uniform cross-sectional shape and diameter along its length. However, distal end 436 has bulbous end section 438 which is larger in diameter than adjacent end structure 434. Bulbous end section 438 has a generally spherical or ellipsoidal shape, giving shape 430 on the whole a shape which resembles a tadpole. Shape 430 is one continuous shape, having bulbous end section 438 at its distal end. Bulbous end section 438 can be used to house a component of an ISSHD of the disclosed technique which cannot fit inside the section of shape 430 from proximal end 432 to adjacent end structure 434. For example, if at least one capacitor (not shown) is to be included the ISSHD of the disclosed technique, and the at least one capacitor is too large to be encapsulated along the length of shape 430 from proximal end 432 to adjacent end structure 434, then the at least one capacitor may be placed in bulbous end section 438. Additional electronic components may also be placed in bulbous end section 438 for coupling a plurality of capacitors together in order to generate a desired high voltage and specific waveform for a given stimulation therapy to be administered by the ISSHD. It is noted that in shape 430, proximal end 432 may be the distal end first inserted into the patient and distal end 436 may be the proximal end located near an incision made into the patient to insert the ISSHD.

In addition, the cross-sectional shape of the ISSHD may vary or change over length, being different at a distal end as compared to a proximal end of the ISSHD, as shown in shape 450. Shape 450 includes a proximal end 452 and a distal end 454. Unlike shapes 420 and 430, shape 450 has a generally conoid shape along its length. As shown in FIG. 8, in the direction of an arrow 456, the cross-section of the generally tubular or cylindrical shape of shape 450 changes over length, with the diameter of a cross-section of proximal end 452 increasing in the direction of distal end 454. Similar to shape 430, the increase in diameter over length of shape 450 enables larger components to be inserted into an ISSHD having such a shape. Therefore, a capacitor or other large electronic component (both not shown) which would not fit in proximal end 452 may be inserted in distal end 454 which has a larger diameter in its cross-section.

The heart device of the disclosed technique may be embodied as an ISHD. The ISHD of the disclosed technique has a substantially spine-like shape, including a plurality of linked structures or vertebrae-like structures, resembling the vertebral column, or spine, of a human. The spine-liked shape of the ISHD of the disclosed technique can also be described as a snake-like shape or a curved shaped. It is noted that the ISHD of the disclosed technique, as mentioned above also in reference to the ISSD of the disclosed technique, has a unitary structure, in that it is a single unit which includes within it all the elements necessary for providing electrical shocks to the heart as therapy for arrhythmias. Unlike the prior art, no leads or additional elements are attached to the ISHD once it is implanted inside a patient. In addition, the ISHD as explained below, is substantially electrically insulated (except for electrodes and sensors placed on its outer surface) and thus does not act as an electric pole, as is the case in prior art ICDs that include an electrically active can. The ISHD of the disclosed technique is further described below in FIGS. 9A to 11B.

Reference is now made to FIGS. 9A and 9B which are schematic illustrations of another injectable subcutaneous heart device (as mentioned above, abbreviated as ISHD), generally referenced 480 and 520 respectively, constructed and operative in accordance with another embodiment of the disclosed technique. ISHDs 480 and 520 are similar to ISSHD 100 (FIG. 2A) and can perform the same functions as ISSHD 100. ISHDs 480 and 520 however have a slightly different construction and structure than ISSHD 100 as explained below. With reference now to FIG. 9A, ISHD 480 includes a plurality of capacitors 482, a plurality of electronic components 484, a plurality of batteries 486, a pair of electrodes 488, a pair of sensors 492 and an interconnecting bus 498. According to another embodiment (not shown) of the disclosed technique, the ISHD includes at least one capacitor, at least electronic component and at least one battery, while also including a plurality of electrodes and a plurality of sensors. Plurality of capacitors 482, plurality of electronic components 484, plurality of batteries 486, pair of electrodes 488 and pair of sensors 492 are substantially similar to the capacitors, electronics, batteries, electrodes and sensors described above in reference to FIG. 2A. It is noted that pair of electrodes 488 and pair of sensors 492 can be referred to in general as electrical leads, with pair of electrodes 488 being electrical leads to delivering an electrical shock to a heart (not shown) and with pair of sensors 492 being electrical leads for sensing electrical activity of the heart. Plurality of electronic components 484 includes at least one central processing unit (herein abbreviated CPU), a plurality of coils, at least one switch and other required electrical elements for sensing and monitoring electrical activity in the heart as well as delivering electrical shocks to the heart in the form of defibrillation and/or pacing therapy. Within each one of plurality of electronic components 484, the electrical elements may be arranged in an ASIC or they may be arranged independent of one another. It is noted that ISHD 480 may optionally include a respective anchoring ring (not shown) at each of its ends. Each anchoring ring may be coupled in the vicinity of pair of sensors 492. The anchoring rings can be used when implanting or extracting ISHD 480 in a patient or from a patient to either pull the ISHD into the patient, pull the ISDH out of the patient or to anchor an end of the ISHD while an additional apparatus, such as an introducer, is removed. This is explained in greater detail below in FIGS. 13A-13D.

Each one of plurality of capacitors 482, plurality of electronic components 484 and plurality of batteries 486 is encapsulated in a rigid encapsulation (not labeled). The encapsulations may be made from a strong metal or metal alloy such as titanium. As shown in FIG. 9A, each encapsulation is linked to its neighboring encapsulation by a link 502. Each link 502 is made from a flexible material, such as a polymer, or a flexible metal. Links 502 may be formed using an axis. Links 502 may also be embodied as flexible members. The encapsulations along with links 502 give ISHD 480 a spine-like structure or a linked structure. The human vertebral column is made up of bone structures known as vertebrae. Vertebrae are rigid structures yet are linked together via soft tissue. The soft tissue is flexible and allows the vertebral column ample flexibility in multiple directions, even though individual vertebrae of the vertebral column are rigid. In a similar manner, each encapsulation in ISHD 480, such as the encapsulations for plurality of capacitors 482, plurality of electronic components 484 and plurality of batteries 486, are rigid structures and protect the components encased inside, such as capacitors, batteries and electronic components. However links 502, which couple one encapsulation to the next, are flexible and afford ISHD 480 flexibility in multiple directions. As described below in FIG. 9C, ISHD 480 is coated in a biocompatible, hermetically sealed and electrically insulating coating (not shown in FIG. 9A). A plurality of short insulating sections 490 is shown in FIG. 9A in which the coating is visible (shown in black in FIG. 9A). The ends of ISHD 480 include pair of electrodes 488 and pair of sensors 492. Pair of electrodes 488 includes a plurality of coils 494 wrapped around a section 496 of each end of ISHD 480. Each electrode 488 is insulated from a respective sensor 492 and a respective neighboring battery (not specifically labeled) by a short insulating section 490. Short insulating section 490 continues into section 496. Each end (not specifically labeled) of ISHD 480 is made from a flexible material, such as a polymer or plastic, and substantially has greater flexibility than the flexibly of the spine-like structure of ISHD 480. As shown, since pair of electrodes 488 must provide electrical shocks to the heart and pair of sensors 492 must sense electrical activity of the heart, these components are placed on the outer surface of ISHD 480, on top of the aforementioned coating. Since these components come in direct contact with the tissue and fluids of the body when ISHD 480 is implanted in a patient, they must be made from metals, or metal alloys, which are at minimum biocompatible.

As shown, the various components of ISHD 480 are coupled physically via links 502. In addition, the electrical components of ISHD 480, such as plurality of capacitors 482 (or at least one capacitor), plurality of electronic components 484 (or at least one electronic component), plurality of batteries 486 (or at least one battery) and pair of electrodes 488 are electrically coupled via interconnecting bus 498. Interconnecting bus 498 can substantially be a conduit in which wires are encapsulated that couple the various components of ISHD 480 electrically. Interconnection bus 498 can also be a multi-wire electrical cable (not shown). As shown, a plurality of electrical links 500 coupled interconnecting bus 498 to each component of ISHD 480. It is noted that the electrical link (not labeled) which couples interconnecting bus 498 to pair of electrodes 488 may also couple pair of sensors 492. For example, a hollow (not shown) in the flexible material constituting the ends of ISHD 480 may enable separate wires (not shown) to be passed there through from pair of sensors 492 and pair of electrodes 488. In this respect, both pair of sensors 492 and pair of electrodes 488 are coupled with interconnecting bus 498 yet remain electrically insulated from one another. In addition, in one embodiment of the disclosed technique, interconnecting bus 498 may include at least one low voltage cable and at least one high voltage cable. The at least one low voltage cable is for transferring signals, such as from pair of sensors 492 to a CPU encapsulated in one of plurality of electronic components 484. The at least one high voltage cable is for delivering electricity to pair of electrodes 488 to provide an electric shock to the heart as therapy.

In FIG. 9A, plurality of capacitors 482 includes four capacitors, plurality of electronic components 484 includes two electronic components and plurality of batteries 486 includes two sets of five batteries each. The particular number of these components as well as their arrangement is FIG. 9A is merely brought as an example. ISHD 480 may include fewer than four or more than four capacitors (not shown). ISHD 480 may include a single encapsulation for electronic components or a plurality of encapsulations for electronic components (not shown). ISHD 480 may include fewer than five batteries per battery set or more than five batteries per battery set (not shown). In addition, the particular arrangement of components as shown in FIG. 9A is merely brought as an example. Plurality of batteries 486 may be interspersed between plurality of capacitors 482 and plurality of electronic components 484. The particular arrangement of batteries, capacitors and electronic components in ISHD 480 is a matter of design choice and is obvious to one skilled in the art. However, pair of sensors 492 and pair of electrodes 488 need to be positioned at the ends of ISHD 480 to properly sense electrical activity of the heart and to give electrical shocks as therapy for various heart arrhythmias.

In the embodiment shown in FIG. 9A, a dotted line 504 divides ISHD 480 into two halves, shown by a plurality of arrows 506A and 506B. Each half of ISHD 480 is symmetric along its length. In addition, ISHD 480 has a generally circular or cylindrical cross-section, with pair of electrodes 488 and pair of sensors 492 embodied as rings or coils. In one embodiment of the disclosed technique, pair of sensors 492 is embodied as a pair of sensing rings (not shown). The cross-section of ISHD 480 may also be substantially symmetric. This arrangement of ISHD 480 enables it to be indifferent to its roll position. Thus interconnecting bus 498 can face the heart of the patient or away from the heart of the patient once implanted. The outer surface of ISHD 480 has no particular directionality and ISHD 480 can be implanted in the patient regardless of which direction its outer surface faces. This is due in part to the circular nature of pair of sensors 492 and pair of electrodes 488.

According to another embodiment (not shown) of the disclosed technique, ISHD 480 may include additional sensors, electrodes or both. These additional sensors, electrodes or both may use different sensing methods (i.e., other than sensing electrical activity) to sense quantifiable parameters of the heart's activity as well as the rhythm and amount of blood flow entering and exiting the heart. For example, the additional sensors may include at least one acoustic sensor or a pair of acoustic sensors, made from a piezoelectric material to detect sonic (i.e., sound) activity of the heart, such as the heart rate. The at least one acoustic sensor or the pair of acoustic sensors may function as standalone units or may work in conjunction with pair of sensors 492 for detecting electrical activity of the heart, sonic activity of the heart or a combination of the two. Doppler shifts in the flow of blood in the aorta (not shown) of a patient can be measured with such sensors either from the mechanical pulsations of the aorta directly, of the heart or both.

With reference now to FIG. 9B, ISHD 520 is substantially similar to ISHD 480 (FIG. 9A), ISHD 520 having similar elements to ISHD 480. Most reference numbers from FIG. 9B are omitted for the purposes of clarity, with equivalent elements between FIGS. 9A and 9B being shaded using equivalent shading. ISHD 520 differs from ISHD 480 in two respects and represents another arrangement and configuration of the ISHD of the disclosed technique. First, ISHD 520 includes six sensors instead of one pair of sensors. As shown, ISHD 520 includes a pair of sensors 522, located at the extremities of ISHD 520, similar to pair of sensors 492 (FIG. 9A). ISHD 520 also includes additional sensors 524A-524D. Additional sensors 524A-524D are substantially similar to pair of sensors 522 and can be embodied having a circular or ring-like shape. Like pair of sensors 522, additional sensors 524A-524D can detect and sense electrical activity of the heart, providing signals to a CPU (not shown) for the determination of whether electrical shocks should be provided to the heart of a patient or not. Whereas two sensors are sufficient to provide ample information about electrical activity of the heart, the signals received by a given pair of sensors may contain noise due to the presence of electrical activity coming from other organs, muscles or tissues around the area of the heart. The noise may cause the ISHD of the disclosed technique to register a false positive. A false positive in this respect refers to sensed electrical activity by, for example, pair of sensors 522 and the subsequent administering of an electrical shock to the heart when the source of the electrical activity was not from the heart. Muscles, tissue and other organs around the heart may also use electrical signals to function and such signals can be detected by the sensors of ISHD 520. A reduction in false positives can be achieved by the disclosed technique by providing a plurality of sensors located along the length of ISHD 520. As shown, additional sensors 524A and 524D are positioned between a respective electrode (not labeled) and a respective battery (not labeled). Additional sensors 524B and 524C are positioned between a respective battery (not labeled) and a respective electronic component (not labeled). Thus the additional sensors are spread out along the length of ISHD 520. In ISHD 520, any two sensors can be used as a pair of sensors to sense electrical activity of the heart, such as pair of sensors 522, additional sensors 524A and 524C, one of pair of sensors 522 and additional sensor 524B and the like. Once ISHD 520 is implanted in a patient, the physician may be able to program which sensors are to be used to determine electrical activity of the heart. Additional equipment, such as electrocardiography equipment, may be used to verify and validate when electrical activity is coming from the heart and the physician may try different pairs of sensors until an optimal pair is selected in which false positives are at a minimum due to electrical activity from sources in the body other than the heart. As mentioned above, ISHD 522 does not need to have six sensors specifically as shown. The location of additional sensors 524A-524D is brought merely as an example, as other arrangements of the additional sensors along the length of ISHD 520 are possible. In addition, ISHD 520 may include only one additional sensor, two additional sensors and the like and not necessarily four additional sensors as shown in FIG. 9B.

The second difference shown between ISHD 480 and ISHD 520 is how the various spine-like structures of ISHD 520 are physically and mechanically coupled to one another. In ISHD 480, each element, be it a battery, capacitor or electronic component, is coupled to its neighboring element by a plurality of links 502 (FIG. 9A), where the links are located in the center of each element. As shown in FIG. 9B, the location of each physical link coupling neighboring encapsulations into the spine-like structure of the disclosed technique is variable. Plurality of links 526 is located in the center of each element's encapsulation, however plurality of links 528 is located at the corner of each element's encapsulation. In the example of FIG. 9B, similar elements, such as the capacitors or the batteries, are linked together by links that couple each element at its corner, as shown in plurality of links 528. Different elements are coupled together via links that are more centrally positioned, as shown in plurality of links 526. For example, additional sensor 524C is coupled to a neighboring battery (not labeled) and electronic component (not labeled) via centrally located plurality of links 526. This arrangement is merely brought as an example and other possibilities of the position of a given link between neighboring elements are possible and a matter of design choice. Differences between a more centrally located link and a link located at an edge of an element are shown and described below in FIGS. 11A and 11B.

Reference is now made to FIG. 9C which is a schematic illustration of the injectable subcutaneous heart device of FIG. 9A with a coating, generally referenced 550, constructed and operative in accordance with a further embodiment of the disclosed technique. ISHD 550 is substantially similar to ISHD 480 (FIG. 9A) and ISHD 520 (FIG. 9B). As shown, ISHD 550 includes a plurality of capacitors 558, a plurality of electronic components 556, a plurality of batteries 554, an interconnecting bus 564, a pair of electrodes 560 and a pair of sensors 562. Once an ISHD has been assembled, a coating 552 is placed on the ISHD, resulting in ISHD 550. In one embodiment, coating 552 may be placed on ISHD 550 by spraying it on. In another embodiment, coating 552 may be placed on ISHD 550 by dunking ISHD 550 in a bath of the coating material. The coating material constituting coating 552 substantially shields and encapsulates all the elements of ISHD 550. A suitable coating material for coating 552 must meet the following criteria:

1. be biocompatible so the outer surface of the ISHD (i.e., the coating) does not cause an inflammatory or reactionary response from the patient's immune system into whom it is implanted;
2. provide electromagnetic immunity (herein abbreviated as EMI) as well as electrical insulation so that the inner components of ISHD 550 do not conduct any electricity outside coating 552 and no electrical activity outside ISHD 550 enters ISHD 550 except through the sensors and the pair of electrodes; and
3. hermetically seal ISHD 550 from the fluids, tissues and other mobile matter in the body of the patient which is in the vicinity of ISHD 550 once implanted.

Coating 552 should also be smooth such that the outer surface of ISHD 550 is smooth and can be easily inserted inside a patient. Coatings meeting the above listed criteria are known and can be obtained from companies such as the Dymax Corporation (www.dymax.com) or similar companies. In one embodiment coating 552 may also provide additional mechanical protection of the inner elements of ISHD 550. In general, coating 552 does not hinder the flexibility of ISHD 550 and should have sufficient flexibility to not tear or rub off as ISHD 550 slightly moves in a patient as the patient goes about his or her daily activities. In one embodiment, pair of sensors 562 and pair of electrodes 560, as they are positioned on the outer surface of ISHD 550, are installed after coating 552 has been applied to ISHD 550. In another embodiment, pair of sensors 562 and pair of electrodes 560 are initially coated in coating 552. Coating 552 is then partially etched away over the areas of pair of sensors 562 and pair of electrodes 560, thus exposing them to the outer surface. As can be seen in FIG. 9C, coating 552 substantially conforms to the shape of the individual components constituting ISHD 550. Nevertheless, coating 552 provides a smooth outer surface of ISHD 550, thus easing its insertion into the body of a patient. It is also noted that in another embodiment of the disclosed technique, coating 552 can be embodied as a shrink wrap or a shrink film meeting the criteria listed above.

Reference is now made to FIGS. 10A, 10B and 100 which are schematic illustrations of different capacitor designs for use in the injectable subcutaneous heart device of FIG. 9A, generally referenced 580, 590 and 600 respectively, constructed and operative in accordance with another embodiment of the disclosed technique. With reference to FIG. 10A, capacitor design 580 includes stacks of capacitors 582 shaped like rectangles, arranged in columns and lined up in series. Each stack of capacitors 582 may be encapsulated in a single encapsulation or alternatively, groups of stacks of capacitors may be encapsulated in a single encapsulation. With reference to FIG. 10B, capacitor design 590 includes a plurality of thin semicircular shaped capacitors 592. Semicircular shaped capacitors 592 may be arranged linearly (shown by the two lower capacitors in FIG. 10B), stacked on top of one another in the same direction (not shown), stacked on top of one another in the reverse direction (as shown in FIG. 10B) or in any other suitable arrangement. With reference to FIG. 10C, capacitor design 600 includes stacks of capacitors 602 shaped like cylinders, arranged in columns and lined up in series. Each stack of capacitors 602 may be encapsulated in a single encapsulation or alternatively, groups of stacks of capacitors may be encapsulated in a single encapsulation. The ISHD of the disclosed technique requires sufficient capacitors to provide a strong enough electric shock to either resynchronize or pace a heart suffering from arrhythmias. It is a matter of design choice in terms of how the capacitors are to be arranged and many other possible capacitor designs are available. According to the disclosed technique, the design of the capacitors is to maximize capacitance while minimizing the amount of space taken up by the capacitors.

Figure 11B:
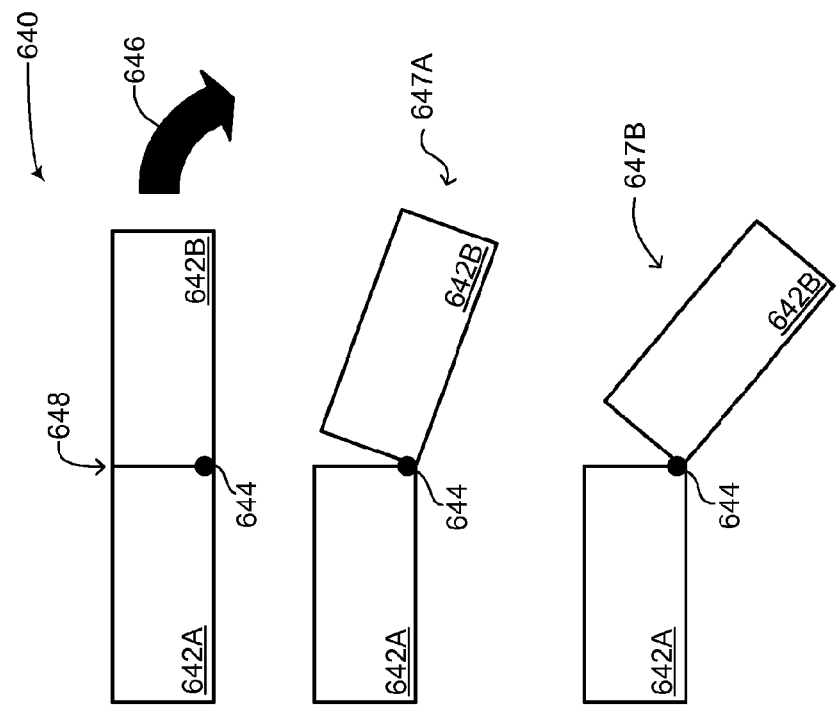
FIGS. 11A and 11B are schematic illustrations of different linking configurations for coupling the various parts of the injectable subcutaneous heart device of FIG. 9A, constructed and operative in accordance with a further embodiment of the disclosed technique.
Figure 11A:
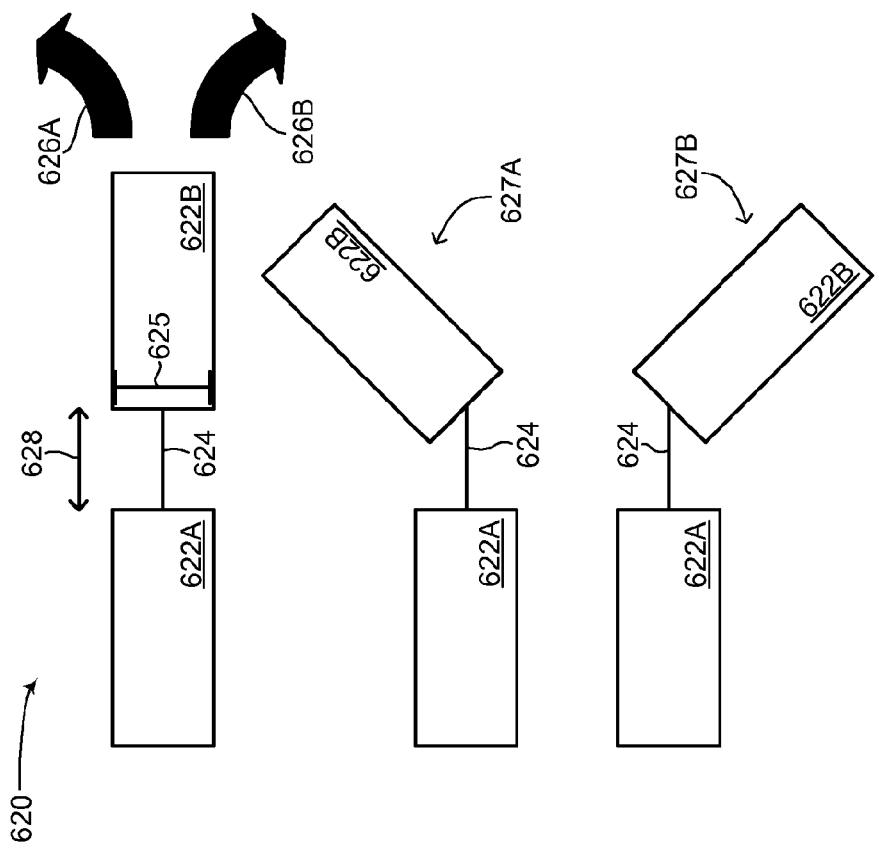

Reference is now made to FIGS. 11A and 11B which are schematic illustrations of different linking configurations for coupling the various parts of the injectable subcutaneous heart device of FIG. 9A, generally referenced 620 and 640 respectively, constructed and operative in accordance with a further embodiment of the disclosed technique. With reference to FIG. 11A, link configuration 620 shows two elements 622A and 622B of the ISHD of the disclosed technique. For illustrative purposes, elements 622A and 622B may be two capacitors, two batteries or a battery and an electronic component, as shown and described above in FIG. 9A. Elements 622A and 622B are linked in the center of their neighboring sides by a link 624. Link 624 separates elements 622A and 622B by a gap 628. Link configuration 620 resembles the configuration of a train, with individual boxcars being linked together at their center. Link 624 enables elements 622A and 622B to turn to the left and the right with respect to one another, as shown by arrows 626A and 626B, thus giving link configuration 620 flexibility even though elements 622A and 622B may be rigid in and of themselves. This is shown via an arrow 627A, showing element 622B turning left with respect to element 622A and via an arrow 627B, showing element 622B turning right with respect to element 622A. A width of elements 622A and 622B is shown by a line 625. If gap 624 is at least half the width of elements 622A and 622B, then elements 622A and 622B can turn a full 90° with respect to one another. A whole train of elements (not shown) can thus have a high degree of flexibility in multiple directions according to link configuration 620. It is noted that link 624 does not need to be placed in the center of the width of elements 622A and 622B. According to link configuration 620, link 624 can be placed anywhere along the width of elements 622A and 622B, including at their corners (not shown). This was shown above in FIG. 9B.

With reference to FIG. 11B, link configuration 640 shows two elements 642A and 642B of the ISHD of the disclosed technique. For illustrative purposes, elements 642A and 624B may be two capacitors, two batteries or a battery and an electronic component, as shown and described above in FIG. 9A. Elements 642A and 642B are linked together at one of their adjoining corners by a link 644. Link 644 may be embodied as a type of hinge. Link 644 causes elements 642A and 642B to be flush against one another, thus affording no gap between them, as shown by an arrow 648. Link configuration 640 enables elements 642A and 642B to turn in only one direction, depending on which corner link 644 is positioned. As shown, link 644 only enables elements 642A and 642B to turn in a rightward direction with respect to one another, as shown by an arrow 646. Link configuration 640 affords elements 642A and 642B a degree of flexibility even though elements 642A and 642B may be rigid in and of themselves. This is shown via an arrow 647A, showing element 642B turning right with respect to element 642A at an angle of 20° and via an arrow 647B, showing element 642B turning further right with respect to element 642A at an angle of 40°. Link 644 enables elements 642A and 642B can turn a full 90° with respect to one another. However unlike link 624 (FIG. 11A), link 644 only enables flexibility in one direction.

In general, either one of link configuration 620 (FIG. 11A) or link configuration 640 can be used according to the disclosed technique to generate the spine-like structure of the ISHD. Link configuration 620 affords the ISHD greater flexibility in multiple directions, however the gap formed between neighboring elements increases the overall length of the ISHD. Link configuration 640 affords the ISHD similar flexibility to link configuration 620, with the ISHD having a shorter overall length, however link configuration 640 limits to flexibility of the ISHD to only one direction. In addition, in link configuration 620, an interconnecting bus (not shown) can be placed on either side of elements 622A and 622B, however the interconnecting bus may experience some excess strain if elements 622A and 622B bend in a manner that stretches the interconnecting bus. In link configuration 640, the interconnecting bus is placed on the side where link 644 is placed. In this respect, the interconnecting bus will not have excess strain placed on it as elements 642A and 642B can only bend in a manner that slightly reduces the length of the interconnecting bus rather than slightly increasing and decreasing it, as can be the case with link configuration 620.

Figure 12:
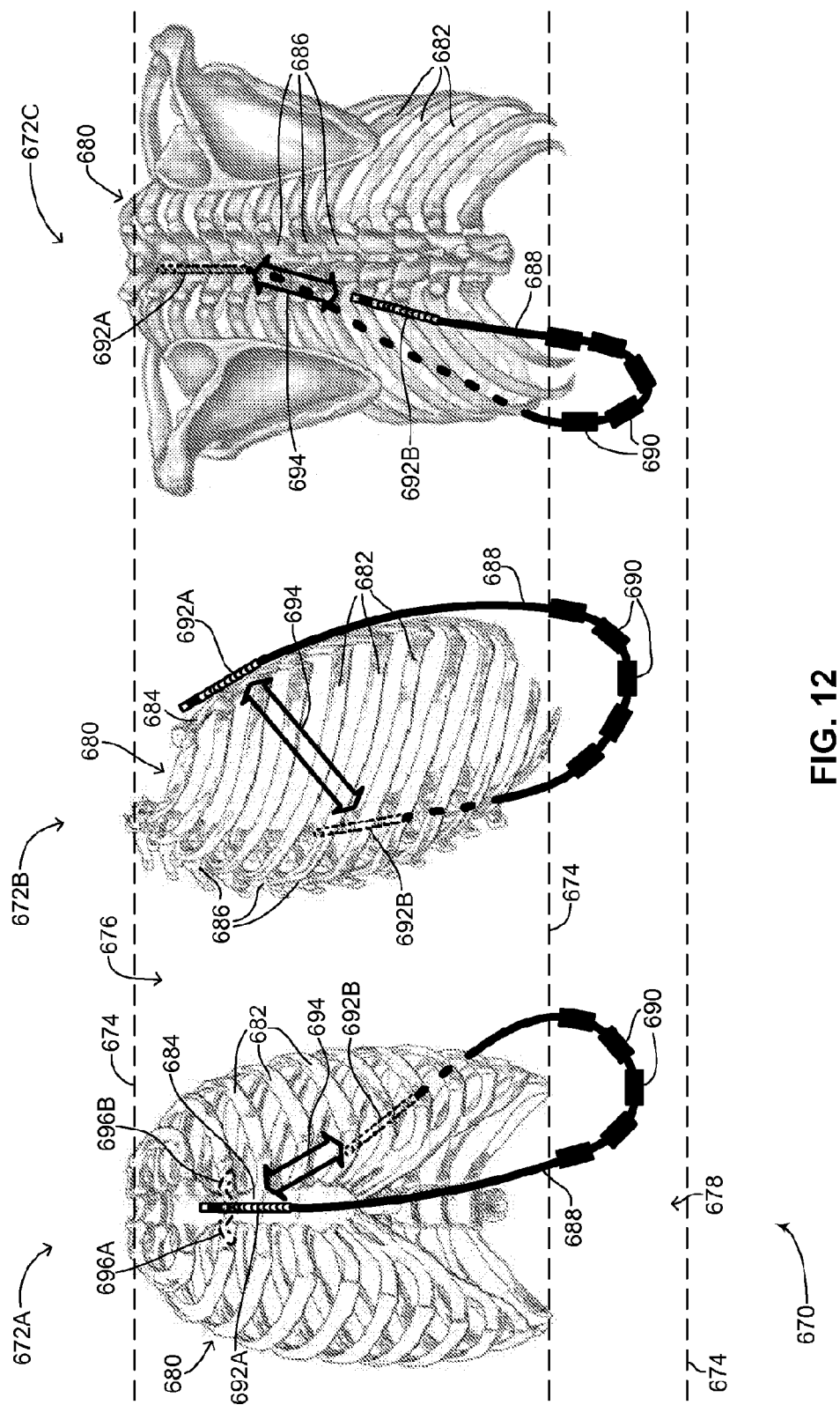
FIG. 12 is a set of orthogonal illustrations showing the placement of the injectable subcutaneous heart device of FIG. 9A in a human patient, constructed and operative in accordance with another embodiment of the disclosed technique.

Reference is now made to FIG. 12 which is a set of orthogonal illustrations showing the placement of the injectable subcutaneous heart device of FIG. 9A in a human patient, generally reference 670, constructed and operative in accordance with another embodiment of the disclosed technique. FIG. 12 shows a ribcage 680 in three different orthogonal illustrations, a front view 672A (also referred to as an anterior view), a side view 672B (also referred to as a lateral view) and a rear view 672C (also referred to as a posterior view). Ribcage 680 is a human ribcage. A set of dotted lines 674 divide a human body (not shown) into a thoracic region 676, where ribcage 680 is located, and an abdominal region 678, where the abdomen and other related organs are situated (not shown). Ribcage 680 includes a plurality of ribs 682, a sternum 684, which is a bony structure on the anterior side of ribcage 680 to which the upper ten of the twelve ribs in thoracic region 676 are coupled to and a plurality of vertebrae 686. Plurality of vertebrae 686 make up the vertebral column (i.e., the spine or spinal column). FIG. 12 shows the placement of an ISHD 688 in a patient (not shown). ISHD 688 is substantially similar to ISHDs 480 (FIG. 9A), 520 (FIG. 9B) and 550 (FIG. 9C). For illustrative purposes not all the elements of ISHD 688 are shown. Shown in ISHD 688 are demonstrative elements 690, which may be capacitors, batteries or electronic components, a pair of electrodes 692A and 692B and a pair of sensors (not labeled). The pair of sensors is located at the respective ends of ISHD 688. As ribcage 680 is shown in a perspective view, elements and parts of ISHD 688 which would be obstructed from view if all organs (not shown) and tissues (not shown) in ribcage 680 were shown are drawn using dotted lines.

As shown in front view 672A, one end of ISHD 688, where electrode 692A is located, is positioned over sternum 684 or on the side of sternum 684. ISHD 688 follows the sternum downwards, and a significant portion of ISHD 688 is positioned in abdominal region 678. ISHD 688 then turns back in thoracic region 676 up to a middle region of plurality of vertebrae 686. Pair of electrodes 692A and 692B is positioned on either side of ribcage 680 such that a depolarization vector 694, generated when an electric shock is administered to a heart (not shown) via pair of electrodes 692A and 692B, passes directly through the heart. The more central depolarization vector 694 is to its path through the heart, the more effect the electric shock administered. As described above, the portion of ISHD 688 over which pair of electrodes 692A and 692B is situated may be made from a more flexible material that the rest of ISHD 688. Thus, the tips (not labeled) of pair of electrodes 692A and 692B, where the pair of sensors is located, may be slightly curved when implanted. For example, the tip of electrode 692A may be slightly curved away from sternum 684 in various positions. Shown in front view 672A are two possible positions for the tip of electrode 692A, a first end position 696A and a second end position 696B. Other end positions are possible for both electrode 692A and electrode 692B. Side view 672B shows how one end of ISHD 688 (the end with electrode 692A) sits on sternum 684 and substantially follows the natural curves of ribcage 680, eventually dipping away from ribcage 680 into abdominal region 678 and returning up the back (not labeled) behind ribcage 680. As seen, depolarization vector 694 is directed straight through ribcage 680 where the heart (not shown) is located. Rear view 672C shows the positioning of electrode 692B about midway up plurality of vertebrae 686.

As shown above in FIGS. 9A-9C, the central portion of the ISHD of the disclosed technique, which includes a plurality of batteries, capacitors and electronic components, may be slightly thicker than the ends of the ISHD where the electrodes and sensors are located. Positioning the central portion of the ISHD in abdominal region 678 instead of thoracic region 676 may provide increased comfort to a patient as abdominal region 678 includes more tissue structures and less bone structures than thoracic region 676. Whereas bone structures are generally rigid, tissue structures are generally malleable and can more easily accommodate the positioning of a device like ISHD 688. The placement of ISHD 688 as shown in FIG. 12 thus enables a more comfortable and aesthetically pleasing positioning of the apparatus inside an individual, causing less trauma and frustration to a patient during his or her daily activities. It is noted that boxed-shaped canisters of prior art ICDs placed in the abdominal region are not liked by patients as the box shape inadvertently puts pressure on the surrounding organs and tissues, making it uncomfortable for patients. The generally round cross-sectional shape of ISHD 688 more naturally mimics the contours of the human body in the abdominal region, thus providing for a more comfortable fit of the apparatus inside a patient. In addition, the placement of ISHD 688, having a spine-like structure or a snake-like structure in the abdominal region will reduce the chances of inadvertent trauma or deformation to the outer structure of ISHD 688 if the outer structure of ISHD 688 suffers some form of trauma or deformation during clinical use, in addition to not exacerbating such trauma or deformation if it occurs. Trauma and deformation may be increased in prior art ICDs which are placed entirely over the ribcage which is substantially a hard rigid surface which little give. Furthermore, the placement of the ISHD of the disclosed technique partially over the ribcage as well as the abdomen enables the ISHD of the disclosed technique to be longer and thicker than would be acceptable if placed solely in the thoracic region. A longer and thicker ISHD might afford more capabilities as well as higher voltage electrical shocks (as there is more room for capacitors) for treating a larger array of arrhythmias.

Figure 13D:
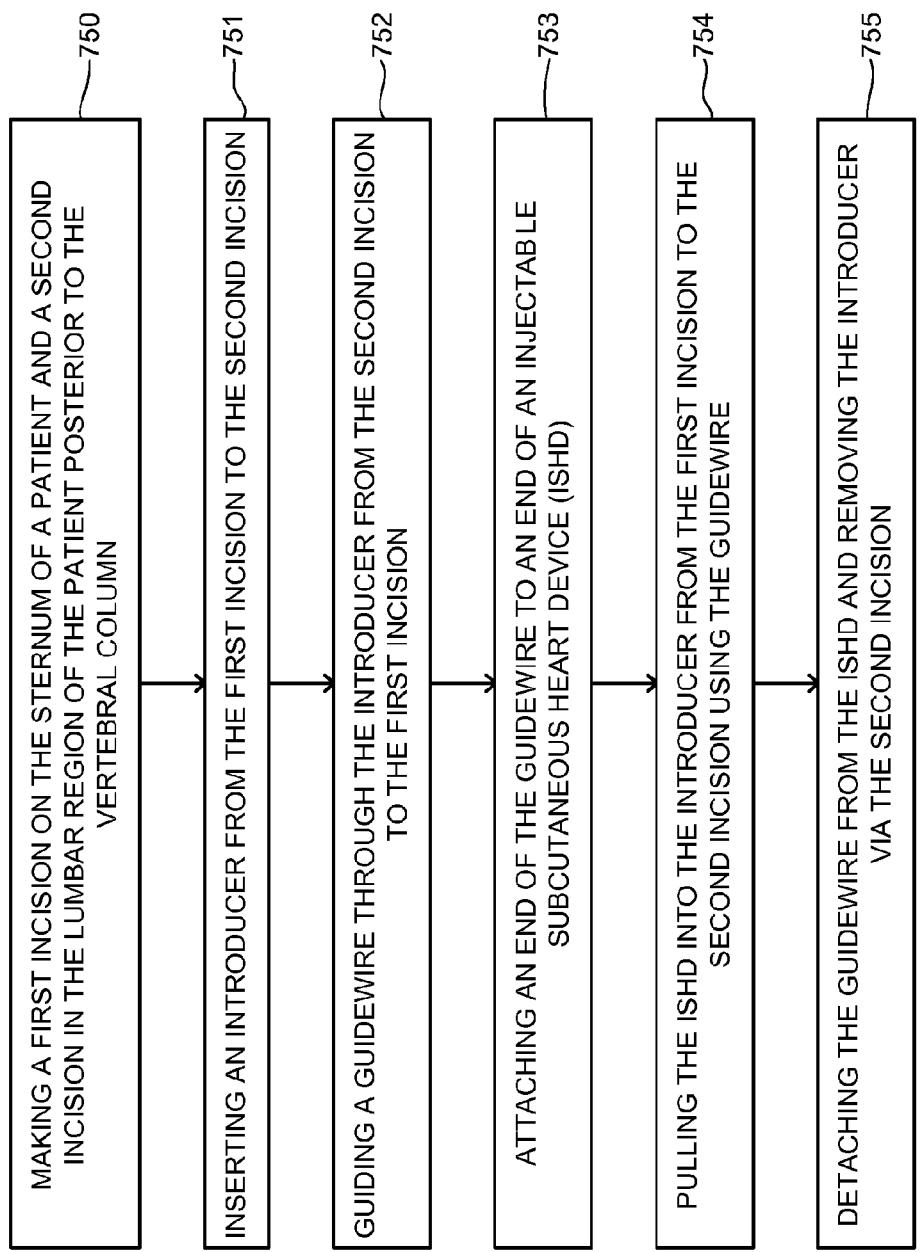

Reference is now made to FIGS. 13A-13D which are schematic illustrations of various methods for implanting an injectable subcutaneous heart device, operative in accordance with a further embodiment of the disclosed technique. Reference is now made to FIG. 13A which shows a first implantation method. In a procedure 720, a small incision is made in the abdomen of a patient. The incision may be between 1-2 centimeters. In a procedure 722, the ISHD of the disclosed technique is folded in half. As explained above, the ISHD of the disclosed technique is quite flexible and malleable due to its spine-like structure. In a procedure 724, a first end of the ISHD is inserted through the incision towards the sternum of the patient and a second end of the ISHD is inserted towards the lower thorax of the patient posterior to the vertebral column. In the method of FIG. 13A, the thicker part of the ISHD is inserted last as the thinner ends of the ISHD are first guided to opposite sides of a patient's ribcage.

Reference is now made to FIG. 13B which shows a second implantation method. In a procedure 730, a small incision is made in the lumbar region of a patient, posterior to the vertebral column. The incision may be between 1-2 centimeters. In a procedure 732, the ISHD of the disclosed technique is folded in half. As explained above, the ISHD of the disclosed technique is quite flexible and malleable due to its spine-like structure. In a procedure 734, via the incision a first end of the ISHD is inserted towards the sternum of the patient and a second end of the ISHD towards the lower thorax of the patient posterior to the vertebral column. Like the method of FIG. 13A, the method of FIG. 13B requires only one incision to be made in a patient for implanting the ISHD of the disclosed technique.

Reference is now made to FIG. 13C which shows a third implantation method. In a procedure 740, a first incision on the sternum of a patient is made and a second incision in the lumbar region of the patient posterior to the vertebral column is also made. The incision on the sternum may be between 0.5-1 centimeters in length whereas the incision in the lumbar region may be between 1-2 centimeters in length. In a procedure 742, a guidewire is guided from the second incision to the first incision. In a procedure 744, an end of the guidewire is attached to an end of the ISHD. In a procedure 746, the ISHD is pulled from the first incision to the second incision using the guidewire, thus positioning it in the patient as shown above in FIG. 12. In the method of FIG. 13C, two incisions are made in the patient.

Reference is now made to FIG. 13D which shows a fourth implantation method. In a procedure 750, a first incision on the sternum of a patient is made and a second incision in the lumbar region of the patient posterior to the vertebral column is also made. The incision on the sternum may be between 0.5-1 centimeters in length whereas the incision in the lumbar region may be between 1-2 centimeters in length. In a procedure 751, an introducer is inserted from the first incision to the second incision. The introducer is substantially a hollow semi-flexible sheath, having a diameter thick enough to enable the ISHD of the disclosed technique to be passed there through. In one embodiment of the disclosed technique, the introducer is substantially as long of the ISHD. In a procedure 752, a guidewire is guided from the second incision to the first incision via the introducer. In a procedure 753, an end of the guidewire is attached to an end of the ISHD. As mentioned above, the ISHD may include at least one anchoring ring. In this procedure, the end of the guidewire is attached to the at least one anchoring ring of the ISHD. In a procedure 754, the ISHD is pulled into the introducer, from the first incision to the second incision, using the guidewire, thus positioning it in the patient as shown above in FIG. 12. In a procedure 755, the guidewire is detached from the ISHD and the introducer is removed from the patient via the second incision. In the method of FIG. 13D, two incisions are made in the patient, similar to the method shown above in FIG. 13C.

In both the methods of FIGS. 13B and 13C, the ISHD may be inserted using an introducer (not shown). The introducer is substantially a sheath or housing covering the ISHD of the disclosed technique, having a thickness of a few millimeters. For example, in FIG. 13B, the ISHD may first be inserted into the introducer and in an alternative to procedure 734, the introducer (with the ISHD inside) is inserted into the patient via the incision towards the sternum of the patient. The ISHD is then held in place while the introducer is removed, thus leaving the ISHD properly positioned. The other (in this method, shorter) end of the ISHD is then inserted through the incision towards the lower thorax of the patient posterior to the vertebral column. In FIG. 13C, the introducer may be pushed from the second incision to the first incision. An end of the ISHD at the first incision is then anchored and the introducer is then removed from the patient via the second incision, thus leaving the ISHD in place in the patient. As mentioned above in FIG. 6C, an injection device or introducer may have a cut or opening along its length enabling the introducer or injection device to accommodate the ISHD if its shape, thickness or both are not substantially symmetric along its length. For example if the ISHD is thicker at its center with its thickness tapering off towards each end, then the introducer or injection device may be designed to have a diameter as thick as the ends of the ISHD (which are the thinnest). The opening along the length of the introducer or injection device can then accommodate the increasing thickness of the ISHD towards its center.

Figure 14:
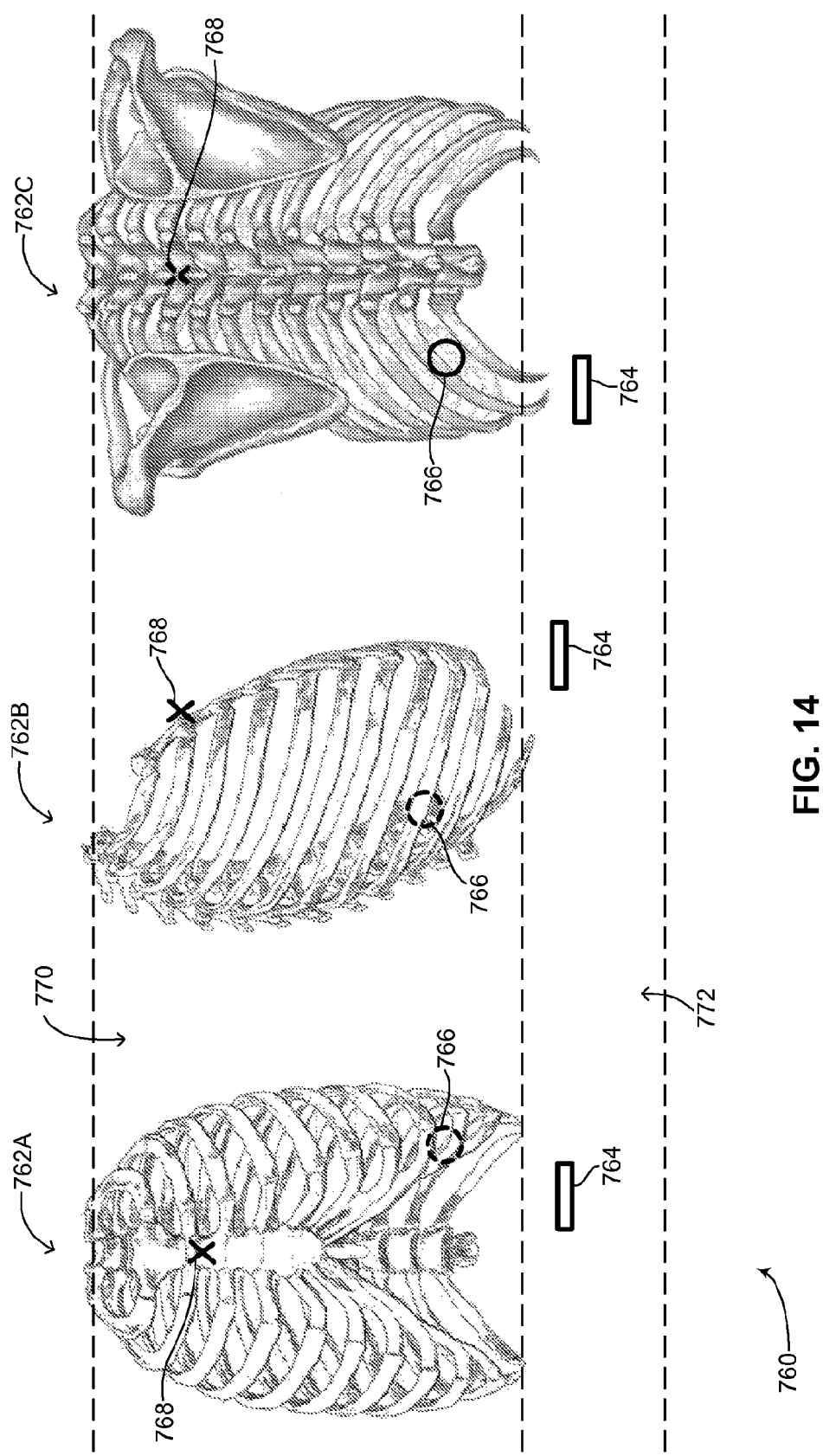
FIG. 14 is a set of orthogonal illustrations showing various insertion marks for implanting an injectable subcutaneous heart device according to the methods of FIGS. 13A-13D, constructed and operative in accordance with another embodiment of the disclosed technique.

Reference is now made to FIG. 14 which is a set of orthogonal illustrations showing various insertion marks for implanting an injectable subcutaneous heart device according to the methods of FIGS. 13A-13D, generally reference 760, constructed and operative in accordance with another embodiment of the disclosed technique. FIG. 14 shows a ribcage (not labeled) in three different orthogonal illustrations, a front view 762A (also referred to as an anterior view), a side view 762B (also referred to as a lateral view) and a rear view 762C (also referred to as a posterior view). Dotted lines divide FIG. 14 into a thoracic region 770 and an abdominal region 772. Different icons in FIG. 14 are used to mark different incision points. The icons are mere position markers and do not represent the shape, length or kind of incision made. As the ribcage in FIG. 14 is drawn in a perspective view, positions which would be obstructed from view if all organs and tissues housed in the ribcage were drawn are drawn using dotted lines. In the method of FIG. 13A, an incision in made in the abdominal region. As shown in FIG. 14 is an abdominal region incision 764, marked using a rectangular icon. In the method of FIG. 13B, an incision in made in the lumbar region. As shown in FIG. 14 is a lumbar region incision 766, marked using a circular icon. In the methods of FIGS. 13C and 13D, two incisions are made in the patient, one of the sternum and the other in the lumbar region. As shown in FIG. 14 is an incision on the sternum 768, marked using an 'X' icon as well as lumbar region incision 766.

It will be appreciated by persons skilled in the art that the disclosed technique is not limited to what has been particularly shown and described hereinabove. Rather the scope of the disclosed technique is defined only by the claims, which follow.

The invention claimed is:

1. Implantable subcutaneous heart device (ISHD) for regulating arrhythmias in a heart of a patient, comprising:
    a plurality of similarly shaped linked structures, each one of said similarly shaped linked structures having a substantially symmetric cross-section;
    an interconnecting bus, for electrically coupling said plurality of similarly shaped linked structures;
    a biocompatible coating, for hermetically sealing and electrically insulating said plurality of similarly shaped linked structures;
    at least two electrodes; and
    a plurality of sensors,
    wherein a first one of said plurality of similarly shaped linked structures encapsulates a power source;
    wherein a second one of said plurality of similarly shaped linked structures encapsulates at least one capacitor;
    wherein a third one of said plurality of similarly shaped linked structures encapsulates electronics;
    wherein said at least two electrodes are respectively placed on an outer surface of at least two different ones of said plurality of similarly shaped linked structures located at opposite ends of said ISHD, for providing electrical shocks to the heart for regulating said arrhythmias and wherein said at least two electrodes each have a substantially symmetric circular cross-section;
    wherein at least two of said plurality of sensors are located on an outer surface at opposite ends of said ISHD, for detecting said arrhythmias in the heart and wherein said plurality of sensors each have a substantially symmetric circular cross-section;
    wherein said at least two electrodes and said plurality of sensors are electrically coupled with said interconnecting bus;
    wherein said power source provides power to said electronics and provides electrical energy to said at least one capacitor;
    wherein said at least one capacitor stores electrical energy and discharges said electrical energy to said at least two electrodes when an arrhythmia is detected in the heart;
    wherein said ISHD is completely positioned subcutaneously around the heart, outside of a ribcage of the patient;
    wherein said plurality of similarly shaped linked structures provides said ISHD flexibility in at least three directions;
    wherein said substantially symmetric circular cross-sections of said at least two electrodes and said plurality of sensors enable said ISHD to be indifferent to its roll position;
    wherein a larger portion of said ISHD is positioned subcutaneously in an abdominal region of the patient.

2. The implantable subcutaneous heart device according to claim 1, wherein said electrical shocks are substantially high voltage defibrillation shocks.

3. The implantable subcutaneous heart device according to claim 1, wherein said electrical shocks are substantially low voltage pacing shocks.

4. The implantable subcutaneous heart device according to claim 1, wherein said ISHD has a substantially circular cross-section.

5. The implantable subcutaneous heart device according to claim 1, wherein said ISHD is a unitary device.

6. The implantable subcutaneous heart device according to claim 1, wherein said electronics comprises:
    at least one central processing unit (CPU);
    a plurality of coils; and
    at least one switch.

7. The implantable subcutaneous heart device according to claim 6, wherein said electronics are arranged in an application specific integrated circuit (ASIC).

8. The implantable subcutaneous heart device according to claim 1, further comprising a respective anchoring ring at each end of said ISHD, each said respective anchoring ring being coupled in a vicinity of a respective one of said plurality of sensors.

9. The implantable subcutaneous heart device according to claim 1, further comprising a respective encapsulation for each one of said plurality of similarly shaped linked structures.

10. The implantable subcutaneous heart device according to claim 9, wherein each said respective encapsulation is made from a material selected from the list consisting of:
    a strong metal; and
    a metal alloy.

11. The implantable subcutaneous heart device according to claim 9, further comprising a plurality of links for respectively coupling said respective encapsulation with a neighboring encapsulation.

12. The implantable subcutaneous heart device according to claim 11, wherein each one of said plurality of links is made from a material selected from the list consisting of:
    a polymer; and
    a flexible metal.

13. The implantable subcutaneous heart device according to claim 11 wherein each one of said plurality of links is centered along each said respective encapsulation.

14. The implantable subcutaneous heart device according to claim 11 wherein each one of said plurality of links is located at a corner along each said respective encapsulation.

15. The implantable subcutaneous heart device according to claim 1, wherein said interconnecting bus is a multi-wire electrical cable.

16. The implantable subcutaneous heart device according to claim 1, wherein said interconnecting bus comprises at least one low voltage cable, for transferring signals and at least one high voltage cable for providing said electrical shocks.

17. The implantable subcutaneous heart device according to claim 1, further comprising at least one additional sensor for detecting at least one of sonic activity of the heart and electrical activity of the heart.

18. The implantable subcutaneous heart device according to claim 17, wherein said sonic activity comprises Doppler shifts in a flow of blood in the heart of the patient.

19. The implantable subcutaneous heart device according to claim 1, wherein said opposite ends of said ISHD are made from a flexible material.

20. The implantable subcutaneous heart device according to claim 19, wherein said flexible material is selected from the list consisting of:
   a polymer; and
   a plastic.

21. The implantable subcutaneous heart device according to claim 1, wherein each one of said plurality of sensors is a sensing ring.

22. The implantable subcutaneous heart device according to claim 1, wherein said plurality of sensors forms at least two sensor pairs, and wherein said at least two sensor pairs are used for reducing false positives in detecting said arrhythmias in the heart.

23. The implantable subcutaneous heart device according to claim 1, wherein said biocompatible coating is placed on said ISHD by a technique selected from the list consisting of:
   spraying on said biocompatible coating;
   dunking said ISHD in a bath of a biocompatible coating material; and
   shrink wrapping said biocompatible coating over said ISHD.

24. The implantable subcutaneous heart device according to claim 1, wherein said biocompatible coating gives an outer surface of said ISHD a smooth surface.

25. The implantable subcutaneous heart device according to claim 1, wherein said biocompatible coating provides mechanical protection of said plurality of similarly shaped linked structures.

26. The implantable subcutaneous heart device according to claim 1, wherein said at least one capacitor has a design selected from the list consisting of:
   stacks shaped like rectangles, arranged in columns and lined up in series;
   a plurality of thin semicircular shapes, arranged linearly;
   a plurality of thin semicircular shapes, stacked on top of one another in a same direction;
   a plurality of thin semicircular shapes, stacked on top of one another in a reverse direction; and
   stacks shaped like cylinders, arranged in columns and lined up in series.

27. Implantable subcutaneous heart device (ISHD) for regulating arrhythmias in a heart of a patient, comprising:
   a plurality of similarly shaped vertebrae-like structures, each one of said similarly shaped vertebrae-like structures having a substantially symmetric cross-section;
   an interconnecting bus, for electrically coupling said plurality of similarly shaped vertebrae-like structures;
   a biocompatible coating, for hermetically sealing and electrically insulating said plurality of similarly shaped vertebrae-like structures;
   at least two electrodes; and
   a plurality of sensors,
   wherein a first one of said plurality of similarly shaped vertebrae-like structures encapsulates a power source;
   wherein a second one of said plurality of similarly shaped vertebrae-like structures encapsulates at least one capacitor;
   wherein a third one of said plurality of similarly shaped vertebrae-like structures encapsulates electronics;
   wherein said at least two electrodes are respectively placed on an outer surface of at least two different ones of said plurality of similarly shaped vertebrae-like structures located at opposite ends of said ISHD, for providing electrical shocks to the heart for regulating said arrhythmias and wherein said at least two electrodes each have a substantially symmetric circular cross-section;
   wherein at least two of said plurality of sensors are located on an outer surface at opposite ends of said ISHD, for detecting said arrhythmias in the heart and wherein said plurality of sensors each have a substantially symmetric circular cross-section;
   wherein said at least two electrodes and said plurality of sensors are electrically coupled with said interconnecting bus;
   wherein said power source provides power to said electronics and provides electrical energy to said at least one capacitor;
   wherein said at least one capacitor stores electrical energy and discharges said electrical energy to said at least two electrodes when an arrhythmia is detected in the heart;
   wherein said ISHD is completely positioned subcutaneously around the heart, outside of a ribcage of the patient;
   wherein said plurality of similarly shaped vertebrae-like structures provides said ISHD flexibility in at least three directions;
   wherein said substantially symmetric circular cross-sections of said at least two electrodes and said plurality of sensors enable said ISHD to be indifferent to its roll position;
   wherein a larger portion of said ISHD is positioned subcutaneously in an abdominal region of the patient.

* * * * *